United States Patent
Banda et al.

(10) Patent No.: US 10,278,986 B2
(45) Date of Patent: May 7, 2019

(54) ANTIBODY-SIRNA CONJUGATES AND USES THEREFOR

(71) Applicant: THE REGENTS OF THE UNIVERSITY OF COLORADO, A BODY CORPORATE, Denver, CO (US)

(72) Inventors: Nirmal Kumar Banda, Aurora, CO (US); V. Michael Holers, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 71 days.

(21) Appl. No.: 15/503,435

(22) PCT Filed: Aug. 3, 2015

(86) PCT No.: PCT/US2015/043359
§ 371 (c)(1),
(2) Date: Feb. 13, 2017

(87) PCT Pub. No.: WO2016/025202
PCT Pub. Date: Feb. 18, 2016

(65) Prior Publication Data
US 2017/0239284 A1   Aug. 24, 2017

Related U.S. Application Data

(60) Provisional application No. 62/037,343, filed on Aug. 14, 2014.

(51) Int. Cl.
| | |
|---|---|
| *A61K 9/00* | (2006.01) |
| *A61K 39/00* | (2006.01) |
| *A61K 47/68* | (2017.01) |
| *C07K 16/28* | (2006.01) |
| *A61K 39/395* | (2006.01) |
| *C12N 15/113* | (2010.01) |
| *A61K 31/7088* | (2006.01) |

(52) U.S. Cl.
CPC ........ *A61K 31/7088* (2013.01); *A61K 9/0019* (2013.01); *A61K 39/3955* (2013.01); *A61K 47/6807* (2017.08); *A61K 47/6849* (2017.08); *C07K 16/2896* (2013.01); *C12N 15/113* (2013.01); *A61K 2039/505* (2013.01); *C07K 2317/76* (2013.01); *C12N 2310/14* (2013.01); *C12N 2310/351* (2013.01); *C12N 2310/3513* (2013.01); *C12N 2320/32* (2013.01)

(58) Field of Classification Search
CPC ............ A61K 31/7088; A61K 47/6849; A61K 9/0019; A61K 47/6807; A61K 39/3955; A61K 2039/505; A61K 2300/00; C12N 15/113; C12N 2320/32; C12N 2310/3513; C12N 2310/14; C12N 2310/351; C07K 16/2896; C07K 2317/76
See application file for complete search history.

(56) References Cited

U.S. PATENT DOCUMENTS

| | | | |
|---|---|---|---|
| 4,196,265 | A | 4/1980 | Croce et al. |
| 4,415,723 | A | 11/1983 | Hedges et al. |
| 4,458,066 | A | 7/1984 | Caruthers et al. |
| 4,554,101 | A | 11/1985 | Hopp |
| 4,816,567 | A | 3/1989 | Cabilly et al. |
| 4,867,973 | A | 9/1989 | Goers et al. |
| 5,399,363 | A | 3/1995 | Liversidge et al. |
| 5,466,468 | A | 11/1995 | Schneider et al. |
| 5,543,158 | A | 8/1996 | Gref et al. |
| 5,565,332 | A | 10/1996 | Hoogenboom et al. |
| 5,580,579 | A | 12/1996 | Ruddy et al. |
| 5,629,001 | A | 5/1997 | Michael et al. |
| 5,641,515 | A | 6/1997 | Ramtoola |
| 5,792,451 | A | 8/1998 | Sarubbi et al. |
| 5,795,715 | A | 8/1998 | Livache et al. |
| 5,889,136 | A | 3/1999 | Scaringe et al. |
| 6,074,674 | A | 6/2000 | Jay et al. |
| 6,270,750 | B1 | 8/2001 | Dioguardi |
| 6,537,514 | B1 | 3/2003 | Prasad et al. |
| 6,613,308 | B2 | 9/2003 | Bartus et al. |
| 6,936,270 | B2 | 8/2005 | Watson et al. |
| 2005/0158406 | A1 | 7/2005 | McPeak et al. |
| 2010/0183516 | A1 | 7/2010 | Ribbert et al. |

(Continued)

FOREIGN PATENT DOCUMENTS

| | | |
|---|---|---|
| EP | 0125023 A1 | 11/1984 |
| EP | 0173494 A2 | 3/1986 |

(Continued)

OTHER PUBLICATIONS

Hauser PV, Pippin JW, Kaiser C, Krofft RD, Brinkkoetter PT, Hudkins KL, Kerjaschki D, Reiser J, Alpers CE, Shankland SJ. Novel siRNA delivery system to target podocytes in vivo. PLoS One. Mar. 1, 2010;5(3):e9463.*

(Continued)

*Primary Examiner* — Rachel B Gill

(74) *Attorney, Agent, or Firm* — Saul Ewing Arnstein & Lehr LLP; Kathryn Doyle; Domingos Silva

(57) ABSTRACT

The disclosure provides compositions and methods relating to the treatment of pain, such as pain from rheumatoid arthritis. By creating conjugates of antibodies that target C5aR and siRNA's that target C5 expression, a dual mode therapeutic that targets two different aspects of C5's inflammatory signaling.

20 Claims, 13 Drawing Sheets
Specification includes a Sequence Listing.

(56) References Cited

U.S. PATENT DOCUMENTS

| | | | |
|---|---|---|---|
| 2013/0123473 A1* | 5/2013 | Goldenberg | A61K 49/0002 530/391.3 |
| 2014/0219956 A1 | 8/2014 | Govindan et al. | |

FOREIGN PATENT DOCUMENTS

| | | |
|---|---|---|
| EP | 0184187 A2 | 6/1986 |
| EP | 0171496 B1 | 5/1993 |
| WO | 8601533 A1 | 3/1986 |
| WO | 8702671 A1 | 5/1987 |
| WO | 0136646 A1 | 5/2001 |

OTHER PUBLICATIONS

Apparailly F, Jorgensen C. siRNA-based therapeutic approaches for rheumatic diseases. Nat Rev Rheumatol. Jan. 2013;9(1):56-62. Epub Oct. 23, 2012.*

Tanaka T, Hishitani Y, Ogata A. Monoclonal antibodies in rheumatoid arthritis:comparative effectiveness of tocilizumab with tumor necrosis factor inhibitors. Biologics. Apr. 7, 2014;8:141-53.*

Hornum L, Hansen AJ, Tornehave D, et al THU0084 C5A and C5AR are Elevated in Joints of Rheumatoid and Psoriatic Arthritis Patients, and C5AR Blockade Attenuates Leukocyte Activation and Migration Annals of the Rheumatic Diseases 2013;72:A191.*

De Paula D, Bentley MV, Mahato RI. Hydrophobization and bioconjugation for enhanced siRNA delivery and targeting. RNA. Apr. 2007;13(4):431-56. Epub Feb. 28, 2007.*

Zhou J, Rossi JJ. Current progress in the development of RNAi-based therapeutics for HIV-1. Gene Ther. Dec. 2011;18(12):1134-8. Epub Sep. 29, 2011.*

LifeSpan BioSciences, Inc. C5AR1/CD88/C5a Receptor Antibody (clone 20/70, Azide free) LS-C62838; accessed Jun. 28, 2018. https://www.lsbio.com/antibodies/c5ar1-antibody-cd88-antibody-c5a-receptor-antibody-clone-20-70-azide-free-flow-ls-c62838/63412#specifications-section.*

Andersson, et al.,T-Cell Receptor VBeta Haplotype and Complement Component C5 Play No Significant Role for the Resistance to Collagen-induced Arthritis in the SWR Mouse, Immun, vol. 73, 1991 ,pp. 191-196.

Banda, et al.,Complement activation pathways in murine immune complex-induced arthritis and in C3a and C5a generation in vitro, Clinical and Experimental Immunology, vol. 159 ,2009 ,pp. 100-108.

Banda, et al.,Mechanisms of Effects of Complement Inhibition in Murine Collagen-Induced Arthritis, Arthritis & Rheumatism, vol. 46, No. 11 ,Nov. 2002 ,pp. 3065-3075.

Banda, et al.,Role of C3a Receptors, C5a Receptors, and Complement Protein C6 Deficiency in Collagen Antibody-Induced Arthritis in Mice, J Immunol, vol. 188 ,2012 ,pp. 1469-1478.

Banerjee, et al.,Influence of complement C5 and V beta T cell receptor mutations on susceptibility tocollagen-induced arthritis in mice, J Immunol, vol. 142 ,1989 ,pp. 2237-2243.

Durigutto, et al.,Prevention of Arthritis by Locally Synthesized Recombinant Antibody Neutralizing Compleent Component C5, PLoS One, vol. 8, No. 3, e58696 ,Mar. 2013 ,pp. 1-8.

Godau, et al.,C5a Initiates the Inflammatory Cascade in Immune Complex Peritonitis, J Immunol, vol. 173 ,2004 ,pp. 3437-3445.

Hill, et al.,Sustained response and long-term safety of eculizumab in paroxysmal nocturnal hemoglobinuria, Blood, vol. 106, No. 7, Oct. 2005 ,pp. 2559-2565.

Kremer, et al.,The Present Status of Research in Burn Toxins, Intensive Care Med, vol. 7, No. 2 ,1981 ,pp. 77-87.

Lee, et al.,Receptors for complement C5a. The importance of C5aR and the enigmatic role of C5L2, Immunol Cell Biol, vol. 86 ,Jan. 2008 ,pp. 153-160.

Li, et al.,C5L2: a controversial receptor of complement anaphylatoxin, C5a, FASEB Journal, vol. 27, No. 3 ,Nov. 2017 ,pp. 855-864.

Lu, et al.,Effect of Necrotic Tissue on Progressive Injury in Deep Partial Thickness Burn Wounds, Chinese Med Journal, vol. 115, No. 3 ,2002 ,pp. 323-325.

Macor, et al.,Treatment of Experimental Arthritis by Targeting Synovial Endothelium With a Neutralizing Recombinant Antibody to C5, Arthritis & Rheumatism, vol. 64, No. 8 ,Aug. 2012 ,pp. 2559-2567.

Mehta, et al.,A New Approach for the Treatment of Arthritis in Mice with a Novel Conjugate of an Anti-C5aR1 Antibody and C5 Small Interfering RNA, J Immunol, vol. 194, No. 11 ,2015 ,pp. 5446-5454.

Nandakumar, et al.,A Recombinant Vaccine Effectively Induces C5a-Specific Neutralizing Antibodies and Prevents Arthritis, PLoS One, vol. 5, No. 10, e13511 ,Oct. 2010 ,pp. 1-11.

Neumann, et al.,Local Production of Complement Proteins in Rheumatoid Arthritis Synovium, Arthritis & Rheumatism, vol. 46, No. 4, Apr. 2002 ,pp. 934-945.

Onuma, et al.,Expression of the anaphylatoxin receptor C5aR (CD88) by human articular chondrocytes, Rheumatol Int, vol. 22 ,May 2002 ,pp. 52-55.

Shagdarsuren, et al.,C5a Receptor Targeting in Neointima Formation After Arterial Injury in Atherosclerosis-Prone Mice, Circulation, vol. 122 ,2010 ,pp. 1026-1036.

Shushakova, et al.,C5a anaphylatoxin is a major regulator of activating versus inhibitory FcγRs in immune complex-induced lung disease, J Clin Invest, vol. 110, No. 12 ,Dec. 2002 ,pp. 1823-1830.

Soruri, et al.,Characterization of C5aR expression on murine myeloid and lymphoid cells by the use of a novel monoclonal antibody, Immunol Lett, vol. 88 ,Feb. 2003 ,pp. 47-52.

Spinella, et al.,The role of C5 and T-cell receptor Vb genes in susceptibility to collagen-induced arthritis, Immunogenetics, vol. 34, Jan. 1991 ,pp. 23-27.

Vergunst, et al.,Blocking the receptor for C5a in patients with rheumatoid arthritis does not reduce synovial inflammation, Rheumatology, vol. 46 ,Oct. 2007 ,pp. 1773-1778.

Wang, et al.,Anti-C5 monoclonal antibody therapy prevents collagen-induced arthritis and ameliorates established disease, Proc Natl Acad Sci USA, vol. 92 ,Sep. 1995 ,pp. 8955-8959.

Wang, et al.,Disruption of the Complement Anaphylatoxin Receptor C5L2 Exacerbates Inflammation in Allergic Contact Dermatitis, J Immunol, vol. 191 ,Sep. 2013 ,pp. 4001-4009.

Woodruff, et al.,Inhibiting the C5—C5a receptor axis, Mol Immunol, vol. 48 ,May 2011 ,pp. 1631-1642.

Yuan, et al.,Expression of C5aR (CD88) of synoviocytes isolated from patients with rheumatoid arthritis and osteoarthritis, Chinese Med J, vol. 116, No. 9 ,2003 ,pp. 1408-1412.

Zheng, et al.,Gene Silencing of Complement C5a Receptor Using SiRNA for Preventing Ischemia/Reperfusion Injury, Am J Pathol, vol. 173, No. 4 ,2008 ,pp. 973-980.

International Search Report dated Nov. 4, 2015 for PCT International Patent Application No. PCT/US2015/043359.

* cited by examiner

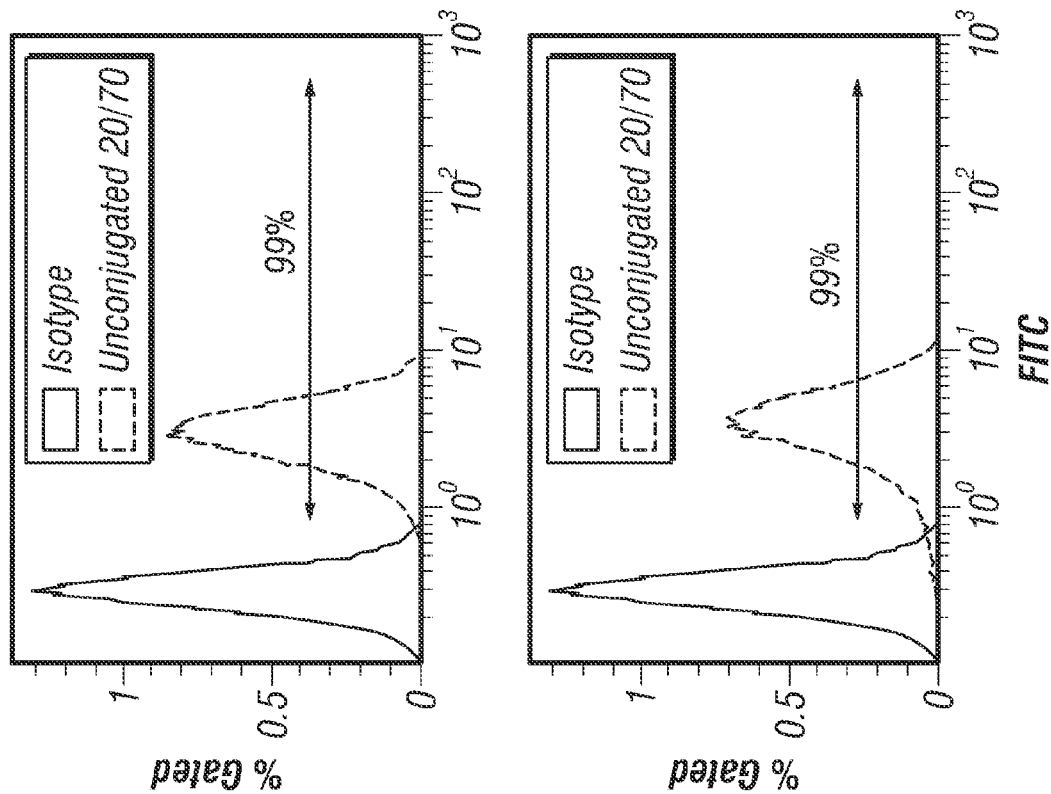
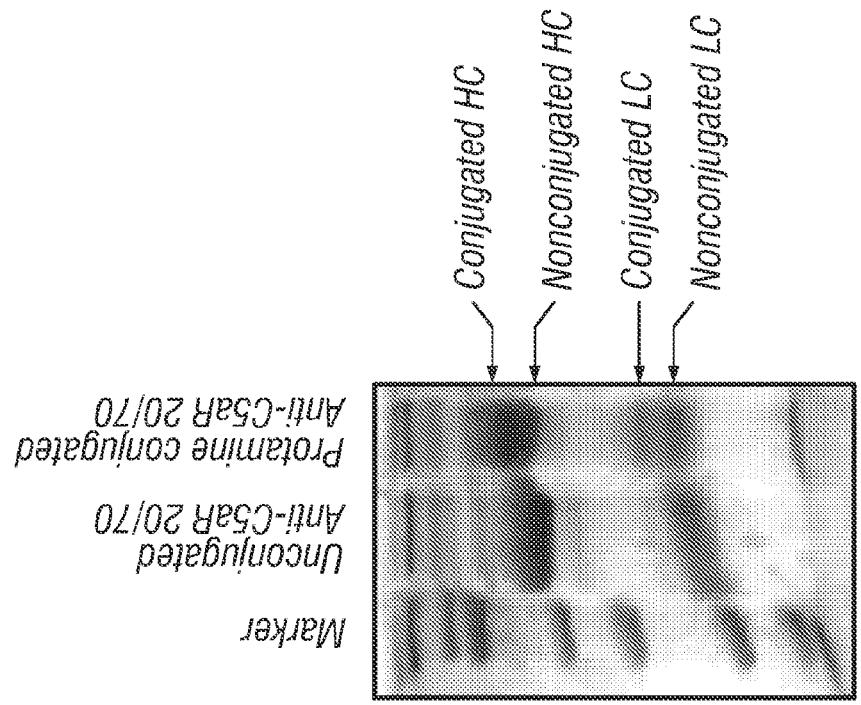
FIG. 3
FIG. 4

| | | | | |
|---|---|---|---|---|
| DNA marker | + | - | - | - |
| Cells/untreated | - | + | - | - |
| Ab/Ctrl siRNA | - | - | + | - |
| Ab/C5 sirRNA | - | - | - | + |

SEQUENCE LISTING

```
<160> NUMBER OF SEQ ID NOS: 1

<210> SEQ ID NO 1
<211> LENGTH: 5448
<212> TYPE: DNA
<213> ORGANISM: Mus musculus

<400> SEQUENCE: 1
```

```
tttaaaagga aagtggttac agggaggcca tgcccatggg tttatgccgc taccagccat      60
gggtctttgg ggaatacttt gtcttttaat tttcctggac aaaacttggg gacaggaaca     120
aacctacgtc atttcagcac ccaaaatcct ccgggtcggc tcgtctgaaa atgtggtaat     180
tcaagtccat ggctacactg aagcatttga tgcaactctt tctctaaaaa gctatcctga     240
caaaaaagtc accttctctt caggctatgt taatttgtcc ccggaaaaca aattccaaaa     300
cgcggcactg ttgacactac agcccaatca agttcctaga aagaaagcc cagtctctca      360
cgtgtatctg gaagttgtgt caaaacactt ttcaaaatca agaaaatac caattaccta      420
taacaatgga attctcttca tccatacaga caaacctgtt tacacgccgg accagtcagt     480
aaagatcaga gtctattctc tgggtgacga cttgaagcca gccaaacggg agactgtctt     540
aactttcata gaccccgaag atcagaagt tgacattgta aagaaaatg attacaccgg       600
aattatctct tttcctgact tcaagattcc atctaatccc aagtatggtg tttggacaat     660
taaagctaac tataagaagg attttacaac aactggaact gcatactttg aaattaaaga    720
atatgtcttg ccacgattct ctgtttcaat agaactagaa agaaccttca ttggctataa    780
aaactttaag aactttgaaa tcactgtgaa agcaagatat ttttataata agtggtacc     840
tgatgctgaa gtgtatgcct ttttggatt gagagaggac ataaaagatg aggagaagca     900
gatgatgcac aaagccacac aagccgcaaa gttggttgac ggagttgctc agatctcttt     960
tgattctgaa acagcagtta aagagctgtc ctacaacagt ctagaagact aaacaacaa    1020
gtacctttat attgcagtaa cagtcacaga atcttcaggt ggattttcag aagaggcaga   1080
aatccctgga gtcaaatatg tcctctctcc ctacacactg aatttggtcg ctactcctct   1140
tttcgtgaag cccgggattc catttttccat caaggcacag gttaaagatt cactcgagca  1200
ggcggtagga ggggtcccag taactctgat ggcacaaaca gtcgatgtga atcaagagac   1260
atctgacttg gaaacaaaga ggagcatcac tcatgacact gatggagtag ctgtgttttgt  1320
gctgaacctc ccatcaaatg tgacggtgct aaagtttgag atcagaactg atgacccaga  1380
acttcccgaa gaaaatcaag ccagcaaaga gtacgaagca gttgcgtact cgtctctcag  1440
ccaaagttac atttacatcg cttggactga aaactacaag cccatgcttg tgggagaata  1500
cctgaatatt atggttaccc ccaagagccc atatatcgac aaaataactc actataatta  1560
cttgatttta tccaaaggca aaattgtaca gtacggcaca agagagaaac ttttctcctc  1620
aacttatcaa aatataaata ttccagtgac acagaacatg gttccttcag cacgactcct  1680
ggtctattac atagtcacag gggagcaaac agcagaatta gtggctgacg cagtctggat  1740
aaatattgag gagaagtgtg gcaaccagct ccaggtccat ctgtctccag atgaatatgt  1800
gtattctcca ggccaaactg tgtcccttga catggtgact gaagcagact catgggtagc  1860
actatcagca gtggacagag ctgtgtataa agtccaggga aacgccaaaa gggccatgca  1920
aagagtcttt caagctttgg atgaaaagag tgacctgggc tgtggggcag gtggtggcca  1980
tgacaatgca gatgtattcc atctagctgg gctcaccttc ctcaccaacg caaacgcaga  2040
tgactcccat tatcgtgatg actcttgtaa agaaattctc aggtcaaaga gaaacctgca  2100
tctcctaagg cagaaaatag aagaacaagc tgctaagtac aaacatagtg tgccaaagaa  2160
atgctgctat gacggagccc gagtgaactt ctacgaaacc tgtgaggagc gagtggcccg  2220
ggttaccata ggccctctct gcatcagggc cttcaacgag tgctgtacta ttgcgaacaa  2280
gatccgaaaa gaaagccccc ataaacctgt ccaactggga aggatccaca ttaagaccct  2340
```

```
gttaccagtg atgaaggcag atatccgaag ctactttcca gagagctggc tatgggaaat    2400
tcatcgcgtt cccaaaagaa aacagctgca ggtcacgctg cctgactcac taacgacttg    2460
ggaaattcaa ggcattggca tttcagacaa tggtatatgt gttgctgata cactcaaggc    2520
aaaggtgttc aaagaagtct tcctggagat gaacatacca tattctgttg tgcgaggaga    2580
acagatccaa ttgaaaggaa ctgtttacaa ctatatgacc tcagggacaa agttctgtgt    2640
taaaatgtct gctgtggagg ggatctgcac ttcaggaagc tcagctgcta gccttcacac    2700
ctccaggccc tccagatgtg tgttccagag gatagagggc tcgtccagtc acttggtgac    2760
cttcaccctg cttcctctgg aaattggcct tcactccata aacttctcac tagagacctc    2820
atttgggaaa gacatcttag taaagacatt acgggtagtg ccagaaggag tcaagaggga    2880
aagctatgcc ggcgtgattc tggaccctaa gggaattcgt ggtattgtta acagacgaaa    2940
ggaattccca tacaggatcc cattagattt ggtccccaag accaaagttg aaaggatttt    3000
gagtgtcaaa ggactgcttg taggggagtt cttgtccacg gttctgagta aggaaggcat    3060
caacatccta acccacctcc ccaagggcag tgcagaggca gagctcatga gcatagctcc    3120
ggtgttctat gttttccact acctggaagc aggaaaccat tggaatattt tctatcctga    3180
tacactgagt aaaagacaga gcctggagaa aaaaataaaa caaggggtgg tgagcgtcat    3240
gtcctacaga aacgctgact attcctacag catgtggaag ggggcgagcg ctagtacctg    3300
gctgacagct tttgctctga gagtgcttgg acaggtggcc aagtatgtaa aacaggatga    3360
aaactcaatt tgtaactctt tgctatggct ggttgagaag tgtcagctgg aaaacggctc    3420
tttcaaggaa aattcccaat atctaccaat aaaattacag ggtactttgc ctgctgaagc    3480
ccaagagaaa actttgtatc ttacagcctt ttctgtgatt ggaattagaa aggcagttga    3540
catatgcccc accatgaaaa tccacacagc gctagataaa gccgactcct tcctgcttga    3600
aaacaccctg ccatccaaga gcaccttcac actggccatt gtagcctatg ctctttccct    3660
aggagacaga acccacccga ggtttcgtct aattgtgtcg gccctgagga aggaagcttt    3720
tgttaaaggt gatccgccca tttaccgtta ctggagagat accctcaaac gtccagacag    3780
ctctgtgccc agcagcggca cagcaggtat ggttgaaacc acagcctatg ctttgctcgc    3840
cagcctgaaa ctgaaggata tgaattacgc caaccccatc atcaagtggc tatctgaaga    3900
gcagaggtat ggaggcggct tttattccac ccaggatacg attaatgcca tcgagggcct    3960
gacagaatat tcactcctgt taaaacaaat tcatttggat atggacatca atgtcgccta    4020
caaacacgaa ggtgacttcc acaagtataa ggtgacagag aagcatttcc tggggaggcc    4080
agtggaggta tctctcaatg atgaccttgt tgtcagcaca ggctacagca gtggcttggc    4140
cacagtatat gtaaaaactg tggttcacaa aattagtgtc tctgaggaat ttgcagcttt    4200
ttacttgaaa attgataccc aagatattga agcatccagc cacttcaggc tcagtgactc    4260
tggattcaag cgcataatag catgtgccag ctacaagccc agcaaggagg agtcaacatc    4320
cgggtcctcc catgcagtaa tggatatatc actgccgact ggaatcggag caaacgagga    4380
agatttacgg gctcttgtgg aaggagtgga tcaactacta actgattacc agatcaaaga    4440
tggccatgtc attctgcaac tgaattcgat ccccctccaga gatttcctct gtgtccggtt    4500
ccggatattt gaacttttcc aagttgggtt tctgaatcct gctaccttca cggtgtacga    4560
gtatcacaga ccagataagc agtgcaccat gatttatagc atttctgaca ccaggcttca    4620
gaaagtctgt gaaggagcag cttgcacatg tgtggaagct gactgtgcgc aactgcaggc    4680
agaagtagac ctagccatct ctgcagactc cagaaaagag aaagcctgta aaccagagac    4740
```

```
tgcatatgct tataaagtca ggatcacatc agccactgaa gaaaatgttt ttgtcaagta    4800
cactgcgact cttctggtca cttacaaaac aggggaagct gctgatgaga attcggaggt    4860
caccttcatt aaaaagatga gctgtaccaa tgccaacctg gtgaaaggga agcagtattt    4920
aatcatgggc aaagaggttc tgcagatcaa acacaatttc agtttcaagt atatataccc    4980
tctagattcc tccacctgga ttgaatattg gcccacagac acaacgtgtc catcctgtca    5040
agcatttgta gagaatttga ataactttgc tgaagacctc ttttttaaaca gctgtgaatg    5100 aaaagttctg ctgcacgaag attcctcctg cggcggggggg attgctcctc ctctggcttg    5160
gaaacctagc ctagaatcag atacactttc tttagagtaa agcacaagct gatgagttac    5220
gactttgtga aatggatagc cttgagggga ggcgaaaaca ggtcccccaa ggctatcaga    5280
tgtcagtgcc aatagactga aacaagtctg taaagttagc agtcaggggt gttggttggg    5340
gccggaagaa gagacccact gaaactgtag ccccttatca aaacatatcc ttgcttgaaa    5400
gaaaaatacc aaggacagaa aatgccataa aatcttgact ttgcactc                5448
```

ANTIBODY-SIRNA CONJUGATES AND USES THEREFOR

This application is a national phase application under 35 U.S.C. § 371 of International Application No. PCT/US2015/043359, filed Aug. 3, 2015, which claims the benefit of priority to U.S. Provisional Application Serial No. 62/037,343, filed Aug. 14, 2014, the entire contents of which are hereby incorporated by reference.

SEQUENCE LISTING

The instant application contains a Sequence Listing which has been submitted in text file format via EFS-Web and is hereby incorporated by reference in it entirety. Said text file was filed on Feb. 13, 2017.

BACKGROUND

I. Field

The present disclosure relates to the fields of molecular biology and medicine. More particularly, it relates to the fields of inflammation and inflammatory disease. Specifically, it deals with the use of antibody-siRNA conjugate to treat rheumatoid arthritis.

II. Related Art

Rheumatoid Arthritis (RA), an inflammatory autoimmune disease of the joints, affects approximately 0.24% of the world population (Cross et al., 2014). This number will rise as the population continues to age. Patients suffering from RA initially experience joint pain which often progresses to joint destruction ultimately leading to the crippling of the patient. It has been estimated that in the U.S., close to 800,000 adults are work-disabled due to this disease (Pincus et al., 1984; Sokka et al., 1999). While the advent of the Biological class of therapeutics has improved outcomes, many patients respond partially or not at all. Thus there is an urgent need for new therapeutics to treat RA.

It is well accepted that complement plays an important role in the development of RA (Ballanti et al., 2013). Of the several components of complement, current evidence points to the component C5 as the most important and strongest inducer of inflammation and the immune response (Woodruff et al., 2011). C5 is cleaved into C5a and C5b. C5a functions as a general activator of inflammatory cells via the C5a receptor (C5aR) while C5b promotes the assembly of the membrane attack complex (MAC, C5b-C9). Several groups generated antibodies or small molecule inhibitors against C5a and C5aR (CD88) which have showed some efficacy in RA in animal models. However, none of these candidate therapeutics have moved from bench to bedside. Therefore, improved clinical interventions in the complement pathway are needed to advance the treatment options for RA.

SUMMARY

Thus, in accordance with the present disclosure, there is provided a composition comprising an antibody that binds immunologically to C5a receptor (C5aR), wherein said C5aR antibody is conjugated to a C5a siRNA. The antibody may be conjugated to said siRNA by a linker, such as a cleavable linker, including that cleaved by an intracellular or extracellular enzyme. The linker may comprise biotin/avidin. The cleavable linker may be cleaved by an agent or treatment exogenous to said subject. The composition may further comprise an inhibitor of C5b, or a second inhibitor of C5a, or an inhibitor of C3a and/or C3b. The composition may further comprise a standard rheumatoid arthritis therapeutic agent.

In another embodiment, there is provided a method of treating a subject having rheumatoid arthritis comprising administering to said subject a composition comprising and antibody that binds immunologically to C5a receptor (C5aR), wherein said C5aR antibody is conjugated to a C5a siRNA. The antibody may be conjugated to said siRNA by a linker, such as a cleavable linker, including that cleaved by an intracellular or extracellular enzyme. The linker may comprise biotin/avidin. The cleavable linker may be cleaved by an agent or treatment exogenous to said subject. The composition may further comprise an inhibitor of C5b, or a second inhibitor of C5a, or an inhibitor of C3a and/or C3b. The composition may further comprise a standard rheumatoid arthritis therapeutic agent.

The administration may comprise oral administration, vascular injection, or intra-articular injection. The method may further comprise administering said composition to said subject at least a second time, such as daily, every other day, every third day, bi-weekly weekly, bi-monthly or monthly administration. The subject may be a human subject or a non-human mammal. The treatment may result in reduced joint pain in said subject, in in greater joint range of motion in said subject, and/or in greater mobility for said subject.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed in this specification can be implemented with respect to any method or composition of the disclosure, and vice versa. Furthermore, compositions and kits of the disclosure can be used to achieve methods of the disclosure.

Throughout this application, the term "about" is used to indicate that a value includes the inherent variation of error for the device, the method being employed to determine the value, or the variation that exists among the study subjects.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 2A) C3aR and C5aR play a role in CAIA. (FIG. 2B) C6 (MAC) play a role on CAIA. (FIG. 2C) C5L2 is dispensable for CAIA. (FIG. 2D) Anti-C5 inhibitory antibody inhibits CAIA.

FIG. 3. Conjugation of 20/70 with protamine. HC: heavy chain. LC: Light chain.

FIG. 4. Comparison of unconjugated and conjugated 20/70 binding to RAW 264.7 cells.

(FIG. 7A) CAIA model. Groups (N=5) injected IP with either PBS, a mix of Anti-C5aR (unconjugated) plus C5siRNA, or equimolar amounts administered as a complex. (FIG. 7B) On day 10 animals were sacrificed. Knee joints from PBS treated and Complex treated tissues were processed for mRNA and various inflammatory genes measured by qPCR using Taqman probes. Data was normalized to 18S rRNA.

(FIGS. 8A-8B) Comparing the CDA and prevalence between WT and C5aR2$^{-/-}$ mice with CAIA CAIA was induced in WT mice with anti-CII mAb 8 mg/mouse injected i.p. on day 0 followed by an i.p. injection of LPS on day 3. Mice were evaluated daily by an observer blinded to the genotype of mouse. (FIG. 8A) Comparison of CDA between WT and C5aR2$^{-/-}$ mice. (FIG. 8B) The prevalence of disease at day 10 in WT and C5aR2$^{-/-}$ mice was 100%. Data shown represent the mean±SEM based on WT, n=5 and C5aR2$^{-/-}$, n=5. No statistically significant differences were seen in the CDA between WT and C5aR2$^{-/-}$ mice. (FIG.8C) CDA in mice injected with either PBS or 750 ug of anti-C5 antibody two times i.e. at day 3 and at day 7. Data shown here represent the mean±SEM based on PBS, n=5 and anti-C5 mAb treatment, n=5 *p<0.05 compared with the CDA in WT mice. CAIA was inhibited by injecting C5 siRNA/C5aR1 siRNA simultaneously but not by alone. (FIGS. 8D-8F) CAIA was induced in WT mice as mentioned above with anti-CII abs and LPS. WT mice were injected with commercially available Accel® siRNAs against C5 or C5aR1 or C5/C5aR1. Groups of 5 mice were input into the CAIA model and treated with I.V. injections of either PBS or C5 siRNA (8 µg) or C5aR1 siRNA (8 µg), or a combination of C5 siRNA and C5aR1 siRNA (16 µg). All data represent the mean±SEM based on n=5 for PBS, n=5 for C5 siRNA, n=5 for C5aR1 siRNA and n=5 for C5 siRNA/C5aR1 siRNA. *p<0.05 in comparison to the PBS or C5 siRNA or C5aR1 siRNA treated mice.

(FIGS. 9A-9C) C5 mRNA levels 72 hours after transduction. (FIG. 9D) C5aR1 mRNA levels 72 hours after transduction. Data was normalized to 18S rRNA. The levels of mRNA expressed in ng/pg. Exact amounts of each mRNA were determined by standard curves generated with synthetic cDNAs. *p<0.05 in comparison to the cells treated with scramble siRNA or untreated cells. Ctrl=Control, Ab=anti-C5aR mAb.

(FIG. 10A) CDA in all treatment groups. (FIG. 10B) Prevalence (%) of disease. (FIGS. 10C-10F) Histopathology, C3 deposition, monocyte/macrophage infiltration, and neutrophil infiltration, at day 10, from the WT mice treated with PBS or a conjugate of anti-C5aR1 mAb-protamine-05 siRNA or with a unconjugate of anti-C5aR1 mAb—no protamine-05 siRNA. (FIG. 10C) Histopathology for inflammation, pannus formation, cartilage damage and bone damage. (FIG. 10D) C3 deposition from all joints in the synovium, on the surface of cartilage and total scores (synovium plus cartilage). (FIG. 10E) Mean score of neutrophils only from the knee joints of mice in all treatment groups. (FIG. 10F) Mean score of macrophages only from the knee joints of mice in all treatment groups. All data represent the mean±SEM based on n=5 for PBS, n=5 for conjugate of anti-C5aR1 mAb-protaimine-05 siRNA and n=5 for anti-C5aR1 mAb—no protamine-05 siRNA. No toxicity was noticed in all treatment groups. *p<0.05 in comparison to the PBS or anti-C5aR1 mAb-protamine with no C5 siRNA.

DETAILED DESCRIPTION

Figure 1:
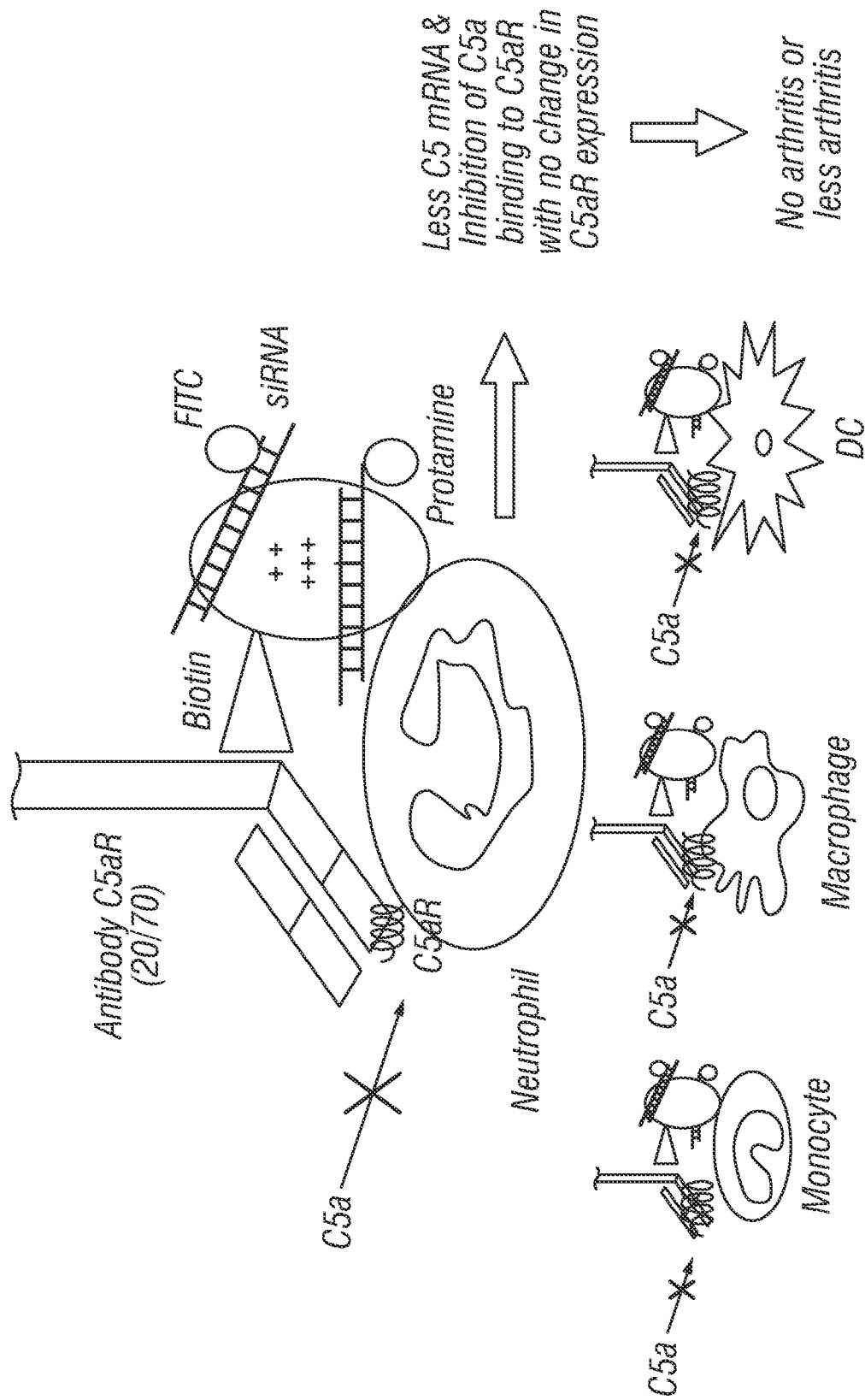
FIG. 1. siRNA-IgG Conjugate with the 4 targeted cell types at bottom of figure.

As discussed above, there is considerable interest in attempting to block certain complement pathways in order to treat rheumatoid arthritis. The inventors have recently shown that while knockout of the C5aR gene results in the complete block of RA in the CAIA model (Banda et al., 2012), an inhibitory anti-C5aR antibody has only limited efficacy. This has led them to propose that inhibition of a single target within the C5-C5aR axis is not sufficient to reproduce the dramatic effects seen in the C5aR gene knockout studies. Here, they describe the double-targeting of C5 expression and C5aR engagement in order to achieve a degree of higher efficacy, closer to that seen in C5aR gene knockout mice. Furthermore, the inventors believe that this strategy will be superior to existing anti-C5 antibodies. Pharmacological block of C5 alone cannot be total and it is possible that the small amount remaining likely will maintain the inflammatory state. Likewise, blockade of C5aR alone cannot be total and competing C5a will activate some small percentage of C5aR. However, the likelihood of activation is proportional to the product of the concentrations of available C5a and C5aR. By blocking both populations, the inventors expect to synergistically decrease the possibility of activation via this pathway. In addition, since the C5-C5aR axis has also been implicated in numerous other inflammatory conditions this therapeutic strategy could have many new potential applications. These and other aspects of the disclosure are set forth in detail below.

I. Complement Components C5a and C5aR In Immune Function and Ra

Complement is a potent effector of innate immunity. Activation may occur via the classical pathway (CP) in which antibodies recognize pathogen surfaces, the lectin pathway (LP) in which lectin binding proteins recognize sugars unique to pathogen surfaces, or the alternative pathway (AP) in which complement auto-catalytically initiates on pathogen surfaces. All pathways converge to form a C3 convertase which cleaves C3 into C3a and C3b. C3b joins the C3 convertase to form the C5 convertase, which then cleaves C5 into C5a and C5b. C3a and C5a are pro-inflammatory molecules which promote the recruitment and activation of inflammatory cells. C3b functions as an opsonin. C5b initiates the formation of the membrane attack complex (MAC, C5b-C9) which promotes pathogen lysis. The C5a receptor (C5aR, CD88), is expressed by immune cells such as neutrophils, dendritic cells and macrophages (Lee et al., 2008), and is also expressed by liver, kidney, brain, lung, and skin (reviewed in (Schieferdecker et al., 2001). Engagement of C5aR results in numerous pro-inflammatory processes including chemotaxis, vasodilation, enhanced secretion of inflammatory mediators and reactive substances, enhanced phagocytosis, as well as other effects (Lee et al., 2008). A second C5a receptor, C5L2 has been identified but its role is controversial (Li et al., 2013). Complement has been implicated in numerous disease states including autoimmune diseases, inflammatory reactions, allergic reactions, asthma, age-related macular degeneration, and cancer (Guo et al., 2005; Hass and van Strijp, 2007; Humbles et al., 2000; Kohl and Wills-Karp, 2000 and Markiewski et al., 2008).

Studies have shown that activated complement components (especially C5) play a central role in joint inflammation in rheumatic diseases. The anti-C5 monoclonal antibody; BB5.1 is capable of decreasing arthritis in the CIA model (Wang et al., 1995). Other C5 neutralizing antibodies prevented both collagen induced arthritis (CIA) and anti-collagen induced arthritis (CAIA) in mice (Nandakumar et al., 2010). C5 deficient mice are highly resistant to CIA in some studies but not others (Andersson et al., 1991; Banerjee et al., 1989; nd Spinella et al., 1991). In a recent study by Macor et al. (Macor et al., 2012) an anti-C5 antibody was developed which bound to mouse, rat, and human RA tissues but not healthy tissues. Clinical effects were modest. Using the CAIA model, the inventors have shown that C3 and C5 components of the complement cascade play an important role in disease development (Banda et al., 2012; Banda et al., 2002 and Banda et al., 2010). Interestingly, they found that over 80% of C5a is derived from the AP (Banda et al., 2010). Their interpretation of these results is that while the complete removal of components of the C5-C5aR axis via gene disruption is capable of profoundly affecting the course of disease, therapeutic inhibition of individual components of complement using inhibitory antibodies is only partially effective.

C5 and C5aR are abundant within human RA joint tissue (Onuma et al., 2002; Yuan et al., 2003 and Neumann et al., 2002). Block of C5aR in human neutrophils using the small molecule inhibitor; PMX53, resulted in a dose dependent block of C5a mediated activation (Vergunst et al., 2007). Clinical trials targeting C5, however, have been unsuccessful. Eculizumab, a humanized anti-C5 antibody showed excellent efficacy when used to treat paroxysmal nocturnal haemoglobinuria (Hill et al., 2005), however, its use in a phase IIb (unpublished) trial for the treatment of RA was unsuccessful (discussed in (Vergunst et al., 2007). PMX53 was also unsuccessful in a small clinical trial testing its efficacy on RA patients (Vergunst et al., 2007). While this might argue against continuing to pursue the C5-C5aR axis as a target there are a number of important deficiencies in the study that decrease its strength in addition to the small number of patients and short study duration. For example, while blood levels of PMX53 were measured, there was no certainty that the drug had entered the synovium. Furthermore, there was no measure of C5 or C5aR levels within synovial tissue. Indeed, when considering their data (see Examples), it is intriguing to note that inhibition of C5aR, combined with knock down of C5a production, appears much more efficacious than inhibition of either C5 or C5aR alone.

II. Antibodies

A. Production Methods

The present disclosure contemplates product and use of antibodies that are immunoreactive with C5aR. The antibody can be a monoclonal antibody, but use of a polyclonal antibody preparation with the same C5aR specificity could be employed. Means for preparing and characterizing antibodies are well known in the art (see, e.g., Harlow and Lane, 1988).

Briefly, polyclonal antibodies are prepared by immunizing an animal with an immunogen (i.e., C5aR or a fragment thereof) and collecting antisera from that immunized animal. A wide range of animal species can be used for the production of antisera. Typically, an animal used for production of antisera is a non-human animal including rabbits, mice, rats, hamsters, pigs or horses. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimido-bencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, i.e., a purified or partially purified C5aR protein, polypeptide or peptide or cell expressing high levels of C5aR. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al. (1977). The use of electrically induced fusion methods is also appropriate (Goding, 1986).

Fusion procedures usually produce viable hybrids at low frequencies, around $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

B. Engineering of Antibody Sequences

In various embodiments, one may choose to engineer sequences of the identified antibodies for a variety of reasons, such as improved expression, improved cross-reactivity, diminished off-target binding or abrogation of one or more natural effector functions, such as activation of complement or recruitment of immune cells (e.g., T cells). The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns. Recombinant full length IgG antibodies can be generated by subcloning heavy and light chain Fv DNAs from the cloning vector into a Lonza pConIgG1 or pConK2 plasmid vector, transfected into 293 Freestyle cells or Lonza CHO cells, and collected and purified from the CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

pCon Vectors™ are an easy way to re-express whole antibodies. The constant region vectors are a set of vectors offering a range of immunoglobulin constant region vectors cloned into the pEE vectors. These vectors offer easy construction of full length antibodies with human constant regions and the convenience of the GS System™.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

It may be desirable to "humanize" antibodies produced in non-human hosts in order to attenuate any immune reaction when used in human therapy. Such humanized antibodies may be studied in an in vitro or an in vivo context. Humanized antibodies may be produced, for example by replacing an immunogenic portion of an antibody with a corresponding, but non -immunogenic portion (i.e., chimeric antibodies). PCT Application PCT/US86/02269; EP Application 184,187; EP Application 171,496; EP Application 173,494; PCT Application WO 86/01533; EP Application 125,023; Sun et al. (1987); Wood et al. (1985); and Shaw et al. (1988); all of which references are incorporated herein by reference. General reviews of "humanized" chimeric antibodies are provided by Morrison (1985); also incorporated herein by reference. "Humanized" antibodies can alternatively be produced by CDR or CEA substitution. Jones et al. (1986); Verhoeyen et al. (1988); Beidler et al. (1988); all of which are incorporated herein by reference.

In related embodiments, the antibody is a derivative of the disclosed antibodies, e.g., an antibody comprising the CDR sequences identical to those in the disclosed antibodies (e.g., a chimeric, humanized or CDR-grafted antibody). In yet a further embodiment, the antibody is a fully human recombinant antibody.

The present disclosure also contemplates isotype modification. By modifying the Fc region to have a different isotype, different functionalities can be achieved. For example, changing to IgG$_4$ can reduce immune effector functions associated with other isotypes.

Modified antibodies may be made by any technique known to those of skill in the art, including expression through standard molecular biological techniques, or the chemical synthesis of polypeptides. Methods for recombinant expression are addressed elsewhere in this document.

One commercially available antibody is clone 20/70 (C5aR-Ab) from LifeSpan Biosciences. Other commercial antibodies include S5/1 and W17/1 from Hycult Biotech, and 8D6 and 3H1740 from Santa Cruz Biotechnology. Thus, in related embodiments, the anti-C5aR antibody is a derivative of one of these antibodies, e.g., an antibody comprising the CDR sequences identical to those mentioned above (e.g., a chimeric, humanized or CDR-grafted antibody). In yet a further embodiment, the anti-C5aR antibody is a fully human recombinant antibody.

III. siRNAs

The present disclosure contemplates the design, synthesis and use of siRNA directed at C5. In other words, these siRNAs will target C5 transcripts to reduce or "silence" C5 expression. siRNAs can be designed according to standard procedures in view of the C5 mRNA sequence, which can be found at NM_010406.2, SEQ ID NO: 1.

RNA interference (also referred to as "RNA-mediated interference" or RNAi) is a mechanism by which gene expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin and Avery et al., 1999; Montgomery et al., 1998; Sharp and Zamore, 2000; Tabara et al., 1999). Activation of these mechanisms targets mature, dsRNA-complementary mRNA for destruction. RNAi offers major experimental advantages for study of gene function. These advantages include a very high specificity, ease of movement across cell membranes, and prolonged down-regulation of the targeted gene (Fire et al., 1998; Grishok et al., 2000; Ketting et al., 1999; Lin and Avery et al., 1999; Montgomery et al., 1998; Sharp et al., 1999; Sharp and Zamore, 2000; Tabara et al., 1999). Moreover, dsRNA has been shown to silence genes in a wide range of systems, including plants, protozoans, fungi, *C. elegans, Trypanasoma, Drosophila*, and mammals (Grishok et al., 2000; Sharp et al., 1999; Sharp and Zamore, 2000; Elbashir et al., 2001). It is generally accepted that RNAi acts post-transcriptionally, targeting RNA transcripts for degradation. It appears that both nuclear and cytoplasmic RNA can be targeted (Bosher and Labouesse, 2000).

siRNAs must be designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., 1998).

The making of siRNAs has been mainly through direct chemical synthesis; through processing of longer, double-stranded RNAs through exposure to *Drosophila* embryo lysates; or through an in vitro system derived from S2 cells. Use of cell lysates or in vitro processing may further involve the subsequent isolation of the short, 21-23 nucleotide siRNAs from the lysate, etc., making the process somewhat cumbersome and expensive. Chemical synthesis proceeds by making two single-stranded RNA-oligomers followed by the annealing of the two single-stranded oligomers into a double-stranded RNA. Methods of chemical synthesis are diverse. Non-limiting examples are provided in U.S. Pat. Nos. 5,889,136, 4,415,723, and 4,458,066, expressly incorporated herein by reference, and in Wincott et al. (1995).

Several further modifications to siRNA sequences have been suggested in order to alter their stability or improve their effectiveness. It is suggested that synthetic complementary 21-mer RNAs having di-nucleotide overhangs (i.e., 19 complementary nucleotides+3' non-complementary dimers) may provide the greatest level of suppression. These protocols primarily use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

Chemically synthesized siRNAs are found to work optimally when they are in cell culture at concentrations of 25-100 nM, but concentrations of about 100 nM have achieved effective suppression of expression in mammalian cells. siRNAs have been most effective in mammalian cell culture at about 100 nM. In several instances, however, lower concentrations of chemically synthesized siRNA have been used (Caplen, et al., 2000; Elbashir et al., 2001).

WO 99/32619 and WO 01/68836 suggest that RNA for use in siRNA may be chemically or enzymatically synthesized. Both of these texts are incorporated herein in their entirety by reference. The enzymatic synthesis contemplated in these references is by a cellular RNA polymerase or a bacteriophage RNA polymerase (e.g., T3, T7, SP6) via the use and production of an expression construct as is known in the art. For example, see U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25mer lengths with the endogenous nuclease complex that converts long dsRNAs to siRNAs in vivo. They do not describe or present data for synthesizing and using in vitro transcribed 21-25mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Preferably, single-stranded RNA is enzymatically synthesized from the PCR products of a DNA template, preferably a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates are preferably attached to a solid surface. After transcription with RNA polymerase, the resulting dsRNA fragments may be used for detecting and/or assaying nucleic acid target sequences.

IV. Treatments

Within the joint, since the major producers of C5 are also activated by C5a, the inventors will utilize chimeric molecules containing C5aR antibodies conjugated to C5 inhibitory siRNA molecules. While antibody-siRNA conjugates have been tested successfully in cell culture, their efficacy in vivo is relatively untested. However, Hauser et al. recently demonstrated that an antibody-siRNA conjugate could successfully inhibit gene expression in podocytes after IV administration in mice (Hauser et al., 2010). Various aspects of these constructs, and their application to the treatment of RA, are discussed below.

A. Rheumatoid Arthritis

Rheumatoid arthritis (RA) is an autoimmune disease that results in a chronic, systemic inflammatory disorder that may affect many tissues and organs, but principally attacks flexible (synovial) joints. It can be a disabling and painful condition, which can lead to substantial loss of functioning and mobility if not adequately treated.

The process involves an inflammatory response of the capsule around the joints (synovium) secondary to swelling (turgescence) of synovial cells, excess synovial fluid, and the development of fibrous tissue (pannus) in the synovium. The pathology of the disease process often leads to the destruction of articular cartilage and ankylosis (fusion) of the joints. RA can also produce diffuse inflammation in the lungs, the membrane around the heart (pericardium), the membranes of the lung (pleura), and white of the eye (sclera), and also nodular lesions, most common in subcutaneous tissue. Although the cause of RA is unknown, autoimmunity plays a big part, and RA is a systemic autoimmune disease. It is a clinical diagnosis made on the basis of symptoms, physical exam, radiographs (X-rays) and labs. About 0.6% of the United States adult population has RA, women two to three times as often as men. Onset is most frequent during middle age, but people of any age can be affected.

1. Risk

Half of the risk for RA is believed to be genetic. It is strongly associated with the inherited tissue type major histocompatibility complex (MHC) antigen HLA-DR4 (most specifically DR0401 and 0404), and the genes PTPN22 and *PADI*4—hence family history is an important risk factor. Inheriting the PTPN22 gene has been shown to double a person's susceptibility to RA. *PADI*4 has been identified as a major risk factor in people of Asian descent, but not in those of European descent. First-degree relatives prevalence rate is 2-3% and disease genetic concordance in monozygotic twins is approximately 15-20%.

Smoking is the most significant non-genetic risk with RA being up to three times more common in smokers than non-smokers, particularly in men, heavy smokers, and those who are rheumatoid factor positive. Modest alcohol consumption may be protective.

Epidemiological studies have confirmed a potential association between RA and two herpesvirus infections: Epstein-Barr virus (EBV) and Human Herpes Virus 6 (HHV-6). Individuals with RA are more likely to exhibit an abnormal immune response to EBV and have high levels of anti-EBV antibodies.

Vitamin D deficiency is common in those with RA and may be causally associated. Some trials have found a decreased risk for RA with vitamin D supplementation while others have not. Vitamin D deficiency is more common in patients with rheumatoid arthritis than in the general population. However, whether vitamin D deficiency is a cause or a consequence of the disease remains unclear. 1α,25-dihydroxyvitamin D3 (1,25D), an active metabolite of vitamin D, effects bone metabolism indirectly through control of calcium and phosphate homeostasis. Interaction between 1,25D and the vitamin D receptor (VDR) effects the production of RANKL and delays osteoclastogenesis.

2. Symptoms

RA primarily affects joints; however it also affects other organs in 15-25% of individuals. It can be difficult to determine whether disease manifestations are directly caused by the rheumatoid process itself, or from side effects of the medications used to treat it—for example, lung fibrosis from methotrexate or osteoporosis from corticosteroids.

Arthritis of joints involves inflammation of the synovial membrane. Joints become swollen, tender and warm, and stiffness limits their movement. With time, multiple joints are affected (it is a polyarthritis). Most commonly involved are the small joints of the hands, feet and cervical spine, but larger joints like the shoulder and knee can also be involved. Synovitis can lead to tethering of tissue with loss of movement and erosion of the joint surface causing deformity and loss of function.

RA typically manifests with signs of inflammation, with the affected joints being swollen, warm, painful and stiff, particularly early in the morning on waking or following prolonged inactivity. Increased stiffness early in the morning is often a prominent feature of the disease and typically lasts for more than an hour. Gentle movements may relieve symptoms in early stages of the disease. These signs help distinguish rheumatoid from non-inflammatory problems of the joints, often referred to as osteoarthritis or "wear-and-tear" arthritis. In arthritis of non-inflammatory causes, signs of inflammation and early morning stiffness are less prominent with stiffness typically less than 1 hour, and movements induce pain caused by mechanical arthritis. The pain associated with RA is induced at the site of inflammation and classified as nociceptive as opposed to neuropathic. The joints are often affected in a fairly symmetrical fashion, although this is not specific, and the initial presentation may be asymmetrical.

As the pathology progresses the inflammatory activity leads to tendon tethering and erosion and destruction of the joint surface, which impairs range of movement and leads to deformity. The fingers may suffer from almost any deformity depending on which joints are most involved. Specific deformities, which also occur in osteoarthritis, include ulnar deviation, boutonniere deformity, swan neck deformity and "Z-thumb." "Z-thumb" or "Z-deformity" consists of hyperextension of the interphalangeal joint, fixed flexion and subluxation of the metacarpophalangeal joint and gives a "Z" appearance to the thumb. The hammer toe deformity may be seen. In the worst case, joints are known as arthritis mutilans due to the mutilating nature of the deformities.

The rheumatoid nodule, which is sometimes cutaneous, is the feature most characteristic of RA. It is a type of inflammatory reaction known to pathologists as a "necrotizing granuloma." The initial pathologic process in nodule formation is unknown but may be essentially the same as the synovitis, since similar structural features occur in both. The nodule has a central area of fibrinoid necrosis that may be fissured and which corresponds to the fibrin-rich necrotic material found in and around an affected synovial space. Surrounding the necrosis is a layer of palisading macrophages and fibroblasts, corresponding to the intimal layer in synovium and a cuff of connective tissue containing clusters of lymphocytes and plasma cells, corresponding to the subintimal zone in synovitis. The typical rheumatoid nodule may be a few millimeters to a few centimeters in diameter and is usually found over bony prominences, such as the olecranon, the calcaneal tuberosity, the metacarpophalangeal joint, or other areas that sustain repeated mechanical stress. Nodules are associated with a positive RF (rheumatoid factor) titer and severe erosive arthritis. Rarely, these can occur in internal organs or at diverse sites on the body.

Several forms of vasculitis occur in RA. A benign form occurs as microinfarcts around the nailfolds. More severe forms include livedo reticularis, which is a network (reticulum) of erythematous to purplish discoloration of the skin caused by the presence of an obliterative cutaneous capillaropathy.

Other, rather rare, skin associated symptoms include pyoderma gangrenosum, Sweet's syndrome, drug reactions, erythema nodosum, lobe panniculitis, atrophy of finger skin, palmar erythema, diffuse thinning (rice paper skin), and skin fragility (often worsened by corticosteroid use).

Fibrosis of the lungs is a recognized response to rheumatoid disease. It is also a rare but well recognized consequence of therapy (for example with methotrexate and leflunomide). Caplan's syndrome describes lung nodules in individuals with RA and additional exposure to coal dust. Pleural effusions are also associated with RA. Another complication of RA is Rheumatoid Lung Disease. It is estimated that about one quarter of Americans with RA develop Rheumatoid Lung Disease.

Renal amyloidosis can occur as a consequence of chronic inflammation. RA may affect the kidney glomerulus directly through a vasculopathy or a mesangial infiltrate but this is less well documented (though this is not surprising, considering immune complex-mediated hypersensitivities are known for pathogenic deposition of immune complexes in organs where blood is filtered at high pressure to form other fluids, such as urine and synovial fluid). Treatment with Penicillamine and gold salts are recognized causes of membranous nephropathy.

People with RA are more prone to atherosclerosis, and risk of myocardial infarction (heart attack) and stroke is markedly increased. Other possible complications that may arise include: pericarditis, endocarditis, left ventricular failure, valvulitis and fibrosis. Many people with RA do not experience the same chest pain that others feel when they have angina or myocardial infarction. To reduce cardiovascular risk, it is crucial to maintain optimal control of the inflammation caused by RA (which may be involved in causing the cardiovascular risk), and to use exercise and medications appropriately to reduce other cardiovascular risk factors such as blood lipids and blood pressure. Doctors who treat RA patients should be sensitive to cardiovascular risk when prescribing anti-inflammatory medications, and may want to consider prescribing routine use of low doses of aspirin if the gastrointestinal effects are tolerable.

3. Diagnosis

Imaging. X-rays of the hands and feet are generally performed in people with a polyarthritis. In RA, there may be no changes in the early stages of the disease, or the x-ray may demonstrate juxta-articular osteopenia, soft tissue swelling and loss of joint space. As the disease advances, there may be bony erosions and subluxation. X-rays of other joints may be taken if symptoms of pain or swelling occur in those joints. Other medical imaging techniques such as magnetic resonance imaging (MRI) and ultrasound are also used in RA.

There have been technical advances in ultrasonography. High-frequency transducers (10 MHz or higher) have improved the spatial resolution of ultrasound images; these images can depict 20% more erosions than conventional radiography. Also, color Doppler and power Doppler ultrasound, which show vascular signals of active synovitis depending on the degree of inflammation, are useful in assessing synovial inflammation. This is important, since in the early stages of RA, the synovium is primarily affected, and synovitis seems to be the best predictive marker of future joint damage.

Blood Tests. When RA is clinically suspected, immunological studies are required, such as testing for the presence of rheumatoid factor (RF, a non-specific antibody). A negative RF does not rule out RA; rather, the arthritis is called seronegative. This is the case in about 15% of patients. During the first year of illness, rheumatoid factor is more likely to be negative with some individuals converting to seropositive status over time. RF is also seen in other illnesses, for example Sjögren's syndrome, hepatitis C, systemic lupus erythematosus, chronic infections and in approximately 10% of the healthy population, therefore the test is not very specific.

Because of this low specificity, new serological tests have been developed, which test for the presence of the anti-citrullinated protein antibodies (ACPAs) or anti-CCP. Like RF, these tests are positive in only a proportion (67%) of all RA cases, but are rarely positive if RA is not present, giving it a specificity of around 95%. As with RF, there is evidence for ACPAs being present in many cases even before onset of clinical disease.

The most common tests for ACPAs are the anti-CCP (cyclic citrullinated peptide) test and the Anti-MCV assay (antibodies against mutated citrullinated Vimentin). Recently a serological point-of-care test (POCT) for the early detection of RA has been developed. This assay combines the detection of rheumatoid factor and anti-MCV for diagnosis of RA and shows a sensitivity of 72% and specificity of 99.7%.

Also, several other blood tests are usually done to allow for other causes of arthritis, such as lupus erythematosus. The erythrocyte sedimentation rate (ESR), C-reactive protein, full blood count, renal function, liver enzymes and other immunological tests (e.g., antinuclear antibody/ANA) are all performed at this stage. Elevated ferritin levels can reveal hemochromatosis, a mimic of RA, or be a sign of Still's disease, a seronegative, usually juvenile, variant of rheumatoid arthritis.

Criteria. In 2010 the 2010 ACR/EULAR Rheumatoid Arthritis Classification Criteria were introduced. These new classification criteria overruled the "old" ACR criteria of 1987 and are adapted for early RA diagnosis. The "new" classification criteria, jointly published by the American College of Rheumatology (ACR) and the European League Against Rheumatism (EULAR) establish a point value between 0 and 10. Every patient with a point total of 6 or higher is unequivocally classified as an RA patient, provided he has synovitis in at least one joint and given that there is no other diagnosis better explaining the synovitis. Four areas are covered in the diagnosis:

joint involvement, designating the metacarpophalangeal joints, proximal interphalangeal joints, the interphalangeal joint of the thumb, second through fifth metatarsophalangeal joint and wrist as small joints, and shoulders, elbows, hip joints, knees, and ankles as large joints:
Involvement of 1 large joint gives 0 points
Involvement of 2-10 large joints gives 1 point
Involvement of 1-3 small joints (with or without involvement of large joints) gives 2 points
Involvement of 4-10 small joints (with or without involvement of large joints) gives 3 points
Involvement of more than 10 joints (with involvement of at least 1 small joint) gives 5 points
serological parameters—including the rheumatoid factor as well as ACPA:
Negative RF and negative ACPA gives 0 points
Low-positive RF or low-positive ACPA gives 2 points
High-positive RF or high-positive ACPA gives 3 points
acute phase reactants:
1 point for elevated erythrocyte sedimentation rate, ESR, or elevated CRP value (c-reactive protein)
duration of arthritis:
1 point for symptoms lasting six weeks or longer The new criteria accommodate to the growing understanding of RA and the improvements in diagnosing RA and disease treatment. In the "new" criteria serology and autoimmune diagnostics carries major weight, as ACPA detection is appropriate to diagnose the disease in an early state, before joints destructions occur. Destruction of the joints viewed in radiological images was a significant point of the ACR criteria from 1987. This criterion no longer is regarded to be relevant, as this is just the type of damage that treatment is meant to avoid.

The criteria are not intended for the diagnosis for routine clinical care; they were primarily intended to categorize research (classification criteria). In clinical practice, the following criteria apply:
two or more swollen joints
morning stiffness lasting more than one hour for at least six weeks
the detection of rheumatoid factors or autoantibodies against ACPA such as
autoantibodies to mutated citrullinated vimentin can confirm the suspicion of RA.

A negative autoantibody result does not exclude a diagnosis of RA.

Differential diagnoses. Several other medical conditions can resemble RA, and usually need to be distinguished from it at the time of diagnosis:
Crystal induced arthritis (gout, and pseudogout)—usually involves particular joints (knee, MTP1, heels) and can be distinguished with aspiration of joint fluid if in doubt.
Redness, asymmetric distribution of affected joints, pain occurs at night and the starting pain is less than an hour with gout.
Osteoarthritis—distinguished with X-rays of the affected joints and blood tests, age (mostly older patients), starting pain less than an hour, a-symmetric distribution of affected joints and pain worsens when using joint for longer periods.
Systemic lupus erythematosus (SLE)—distinguished by specific clinical symptoms and blood tests (antibodies against double-stranded DNA)
One of the several types of psoriatic arthritis resembles RA—nail changes and skin symptoms distinguish between them Lyme disease causes erosive arthritis and may closely resemble RA—it may be distinguished by blood test in endemic areas Reactive arthritis (previously Reiter's disease)—asymmetrically involves heel, sacroiliac joints, and large joints of the leg. It is usually associated with urethritis, conjunctivitis, iritis, painless buccal ulcers, and keratoderma blennorrhagica.

Ankylosing spondylitis—this involves the spine, although a RA-like symmetrical small-joint polyarthritis may occur in the context of this condition.

Hepatitis C—RA-like symmetrical small-joint polyarthritis may occur in the context of this condition. Hepatitis C may also induce Rheumatoid Factor auto-antibodies Rarer causes that usually behave differently but may cause joint pains:

Sarcoidosis, amyloidosis, and Whipple's disease can also resemble RA.

Hemochromatosis may cause hand joint arthritis.

Acute rheumatic fever can be differentiated from RA by a migratory pattern of joint involvement and evidence of antecedent streptococcal infection. Bacterial arthritis (such as *streptococcus*) is usually asymmetric, while RA usually involves both sides of the body symmetrically.

Gonococcal arthritis (another bacterial arthritis) is also initially migratory and can involve tendons around the wrists and ankles.

4. Treatment

There is no cure for RA, but treatments can improve symptoms and slow the progress of the disease. Disease-modifying treatment has the best results when it is started early and aggressively. The goals of treatment are to minimize symptoms such as pain and swelling, to prevent bone deformity (for example, bone erosions visible in X-rays), and to maintain day-to-day functioning. This can often be achieved using two main classes of medications: analgesics such as NSAIDs, and disease-modifying anti-rheumatic drugs (DMARDs). RA should generally be treated with at least one specific anti-rheumatic medication. The use of benzodiazepines (such as diazepam) to treat the pain is not recommended as it does not appear to help and is associated with risks. Analgesics, other than NSAIDs, offer lesser, but some benefit with respect to pain, whilst not causing the same level of gastrointestinal irritation.

Regular exercise is recommended as both safe and useful to maintain muscles strength and overall physical function. It is uncertain if specific dietary measures have an effect.

Disease-modifying anti-rheumatic drugs (DMARD) are the primary treatment for RA. They are a diverse collection of drugs, grouped by use and convention. They have been found to improve symptoms, decrease joint damage, and improve overall functional abilities. They should be started very early in the disease as when they result in disease remission in approximately half of people and improved outcomes overall.

The most commonly used agent is methotrexate with other frequently used agents including sulfasalazine and leflunomide. Sodium aurothiomalate (Gold) and cyclosporin are less commonly used due to more common adverse effects. Agents may be used in combinations.

Methotrexate is the most important and useful DMARD and is usually the first treatment. Adverse effects should be monitored regularly with toxicity including gastrointestinal, hematologic, pulmonary, and hepatic. Side effects such as nausea, vomiting or abdominal pain can be reduced by taking folic acid. The most common undesirable affect is that it increases liver enzymes in almost 15% of people. It is thus recommended that those who consistently demonstrate abnormal levels of liver enzymes or have a history of liver disease or alcohol use undergo liver biopsies. Methotrexate is also considered a teratogenic and as such, it is recommended women of childbearing age should use contraceptives to avoid pregnancy and to discontinue its use if pregnancy is planned.

Biological agents should generally only be used if methotrexate and other conventional agents are not effective after a trial of three months. These agents include: tumor necrosis factor alpha (TNFα) blockers such as infliximab; interleukin 1 blockers such as anakinra, monoclonal antibodies against B cells such as rituximab, T cell costimulation blocker such as abatacept among others. They are often used in combination with either methotrexate or leflunomide.

TNF blockers and methotrexate appear to have similar effectiveness when used alone and better results are obtained when used together. TNF blockers appear to have equivalent effectiveness with etanercept appearing to be the safest. Abatacept appears effective for RA with 20% more people improving with treatment than without. There however is a lack of evidence to distinguish between the biologics available for RA. Issues with the biologics include their high cost and association with infections including tuberculosis.

NSAIDs reduce both pain and stiffness in those with RA. Generally they appear to have no effect on people's long term disease course and thus are no longer first line agents. NSAIDs should be used with caution in those with gastrointestinal, cardiovascular, or kidney problems.

COX-2 inhibitors, such as celecoxib, and NSAIDs are equally effective. They have a similar gastrointestinal risk as an NSAIDs plus a proton pump inhibitor. In the elderly there is less gastrointestinal intolerance to celecoxib than to NSAIDs alone. There however is an increased risk of myocardial infarction with COX-2 inhibitors. Anti-ulcer medications are not recommended routinely but only in those high risk of gastrointestinal problems.

Glucocorticoids can be used in the short term for flare-ups, while waiting for slow-onset drugs to take effect. Injection of glucocorticoids into individual joints is also effective. While long-term use reduces joint damage it also results in osteoporosis and susceptibility to infections, and thus is not recommended.

In early phases of the disease, an arthroscopic or open synovectomy may be performed. It consists of the removal of the inflamed synovia and prevents a quick destruction of the affected joints. Severely affected joints may require joint replacement surgery, such as knee replacement. Postoperatively, physiotherapy is always necessary.

B. Conjugates

As discussed above, the present disclosure envisions the use of bi-functional conjugates containing and antibody function for the immunological binding of C5aR and an siRNA designed to downregulate C5 expression. In order to deliver these two components to the appropriate cell/tissue/joint/disease site, these molecules will be linked together by a chemical moiety. The chemical moiety may be one that is designed to be cleaved following contact of the antibody molecule with the C5aR, such as by an enzyme located outside the cell, on the cell surface or inside the cell, such as in the cytoplasm or vacuole. Alternatively, the linker may be cleaved by an external agent or treatment, such as one provided by a clinician at about the time of treatment (but delayed by a sufficient amount of time for the antibody-binding to take place).

Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidino-, indole-, or carboxyl-specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

In another example, heterobifunctional cross-linking reagents and methods of using the cross-linking reagents are described in U.S. Pat. No. 5,889,155, specifically incorporated herein by reference in its entirety. The cross-linking reagents combine a nucleophilic hydrazide residue with an electrophilic maleimide residue, allowing coupling in one example, of aldehydes to free thiols. The cross-linking reagent can be modified to cross-link various functional groups and is thus useful for cross-linking polypeptides. In instances where a particular peptide does not contain a residue amenable for a given cross-linking reagent in its native sequence, conservative genetic or synthetic amino acid changes in the primary sequence can be utilized.

One kind of linker is a peptide linker (i.e., a short sequence of amino acids that joins two polypeptide domains in a contiguous sequence) or cross-linking agents (chemicals that can covalently two polypeptide domains) may be used to fuse the ADP-ribose binding segment to the constant region (Fc) of human or mouse IgG1 sequences. Peptide mimetics or peptoids can also be used to created linkers.

Another approach to connect two molecules, utilized in the Examples below, is to provide a receptor-ligand pair, and attach one of each to the antibody and siRNA. The "linkage" is then achieved by permitting the receptor-ligand pair to interact. One example of such a receptor-ligand pair is biotin-avidin.

C. Pharmaceutical Compositions and Routes of Administration

Pharmaceutical compositions of the present disclosure comprise an effective amount of a conjugate dissolved or dispersed in a pharmaceutically acceptable carrier. The phrases "pharmaceutical or pharmacologically acceptable" refer to molecular entities and compositions that do not produce an adverse, allergic or other untoward reaction when administered to an animal, such as, for example, a human, as appropriate. The preparation of a pharmaceutical composition that contains at least one conjugate, and optionally an additional active ingredient, will be known to those of skill in the art in light of the present disclosure, as exemplified by Remington's Pharmaceutical Sciences, 18th Ed., Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed., Mack Printing Company, 1990, 1289-1329, incorporated herein by reference). Except insofar as any conventional carrier is incompatible with the active ingredient, its use in the pharmaceutical compositions is contemplated.

The conjugate may be admixed with different types of carriers depending on whether it is to be administered orally or by injection. The present disclosure can be administered buccally, intravenously, intradermally, transdermally, intrathecally, intraarterially, intraperitoneally, intranasally, intravaginally, intrarectally, topically, intramuscularly, intraarticularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., nanoparticles, liposomes), or by other method or any combination of the forgoing as would be known to one of ordinary skill in the art (see, for example, Remington's Pharmaceutical Sciences, 18th Ed. Mack Printing Company, 1990, incorporated herein by reference). In particular, the anti-C5aR antibody is formulated into a syringeable composition for use in intravenous administration.

The conjugate may be formulated into a composition in a free base, neutral or salt form or ester. It may also be synthesized/formulated in a prodrug form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric, fumaric, or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective.

Further in accordance with the present disclosure, the composition of the present disclosure suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of the composition contained therein, its use in administrable composition for use in practicing the methods of the present disclosure is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In a specific embodiment of the present disclosure, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in the composition include buffers, amino acids such as glycine and lysine, carbohydrates such as dextrose, mannose, galactose, fructose, lactose, sucrose, maltose, sorbitol, mannitol, etc.

In further embodiments, the present disclosure may concern the use of a pharmaceutical lipid vehicle composition that include conjugates, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds which contain long-chain aliphatic hydrocarbons and their derivatives. A lipid may be naturally-occurring or synthetic (i.e., designed or produced by man). Lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof.

One of ordinary skill in the art would be familiar with the range of techniques that can be employed for dispersing a composition in a lipid vehicle. For example, the conjugate may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present disclosure administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, conjugate pharmaceutical compositions may comprise, for example, at least about 0.1% of the conjugate, about 0.5% of the conjugate, or about 1.0% of the conjugate. In other embodiments, the conjugate may comprise between about 2% to about 75% of the weight of the unit, or between about 25% to about 60%, for example, and any range derivable therein. Naturally, the amount of the antagonist in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose of conjugate may also comprise from about 0.1 microgram/kg/body weight, about 0.2 microgram/kg/body weight, about 0.5 microgram/kg/body weight, about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In particular embodiments of the present disclosure, the conjugate is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tablets, troches, capsules, elixirs, suspensions, syrups, wafers, and the like (Mathiowitz et al., 1997; Hwang et al., 1998; U.S. Pat. Nos. 5,641,515, 5,580, 579 and 5,792, 451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup or elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration, such as in the treatment of periodontal disease, the compositions of the present disclosure may alternatively be incorporated with one or more excipients in the form of a mouthwash, dentifrice, buccal tablet, oral spray, gel or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet, gel or solution form that may be placed under the tongue, along the gum line, brushed on to teeth surfaces, or otherwise dissolved in the mouth. U.S. Pat. Nos. 6,074,674 and 6,270,750, both incorporated by reference, describe topical, sustained release compositions for periodontal procedures.

In further embodiments, the conjugate may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,537,514, 6,613,308, 5,466,468, 5,543,158; 5,641,515; and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it may be desirable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

D. Combination Treatments

As discussed, the present disclosure provides for the treatment of rheumatoid arthritis. Other agents may be used in combination with the conjugates of the present disclosure for the same therapeutic purpose. This may achieve a greater therapeutic benefit to the patient, and/or may reduce side effects by permitting a lower dose of one or the other agent, or both. More specifically, these agents would be provided in a combined amount (along with the conjugate) to produce any of the effects that either agent might produce on their own. This process may involve contacting the subject with both agents at the same time, such as by contacting the subject with a single composition or pharmacological formulation that includes both agents, or by contacting the subject with two distinct compositions or formulations at the same time.

Alternatively, one agent may precede or follow the other by intervals ranging from minutes to weeks. In embodiments where the agents are applied separately to the subject, one would generally ensure that a significant period of time did not expire between the time of each delivery, such that the agents would still be able to exert an advantageously combined effect on the subject. In such instances, it is contemplated that one may contact the subject with both modalities within about 12-24 h of each other and, more preferably, within about 6-12 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Various combinations may be employed, the conjugate is "A" and the other agent is "B";

| | | | | | | | |
|---|---|---|---|---|---|---|---|
| A/B/A | B/A/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

Administration protocols and formulation of such agents will generally follow those of standard pharmaceutical drugs, as discussed further below.

V. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Results

Figure 2A:
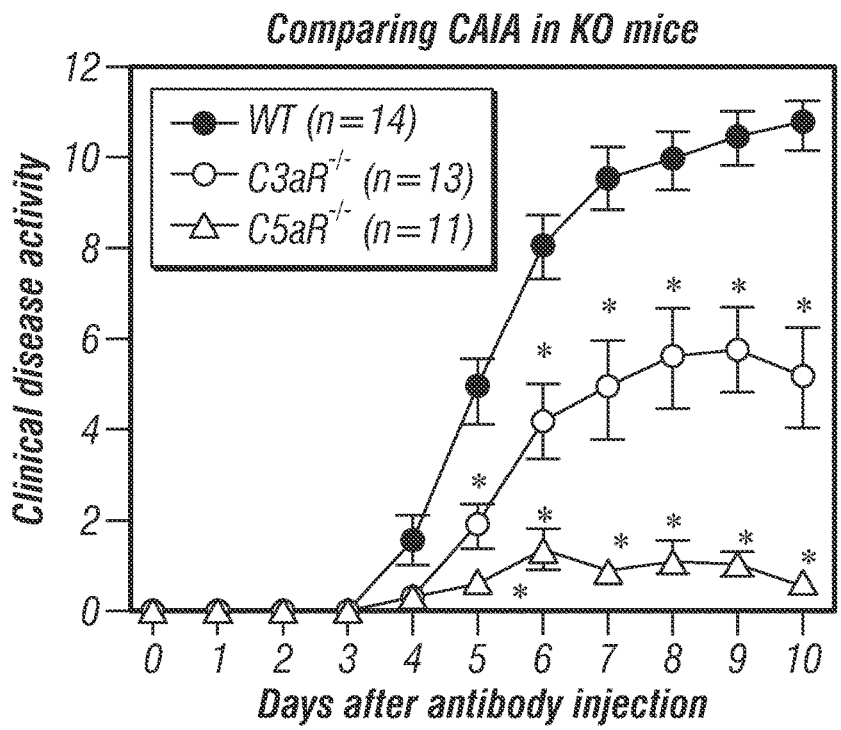
FIGS. 2A-2D. CAIA in various knock out (KO) and deficient mice and effect of an inhibitory antibody on the development of arthritis.
Figure 2B:
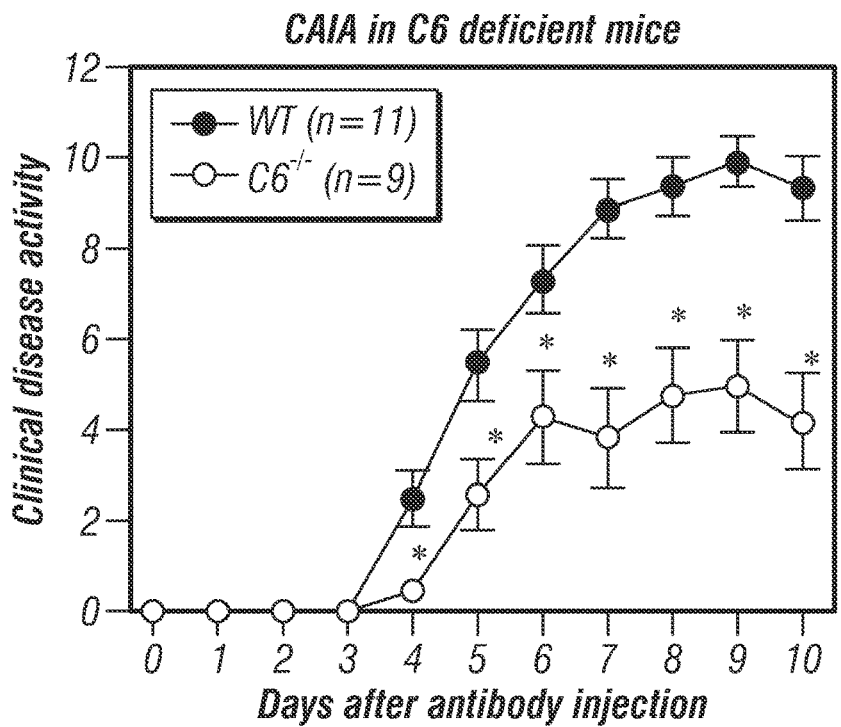
Figure 2C:
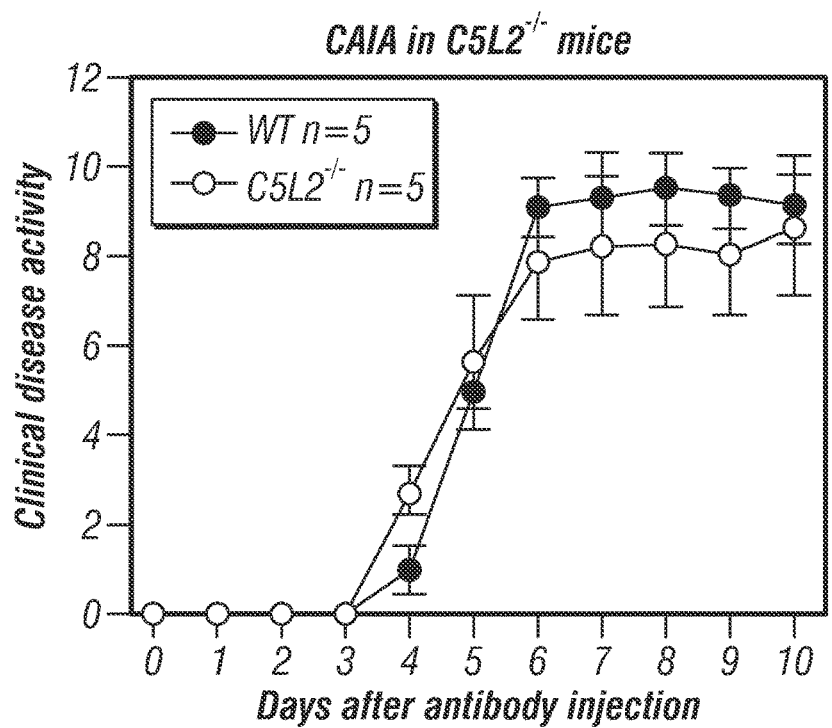
Figure 2D:
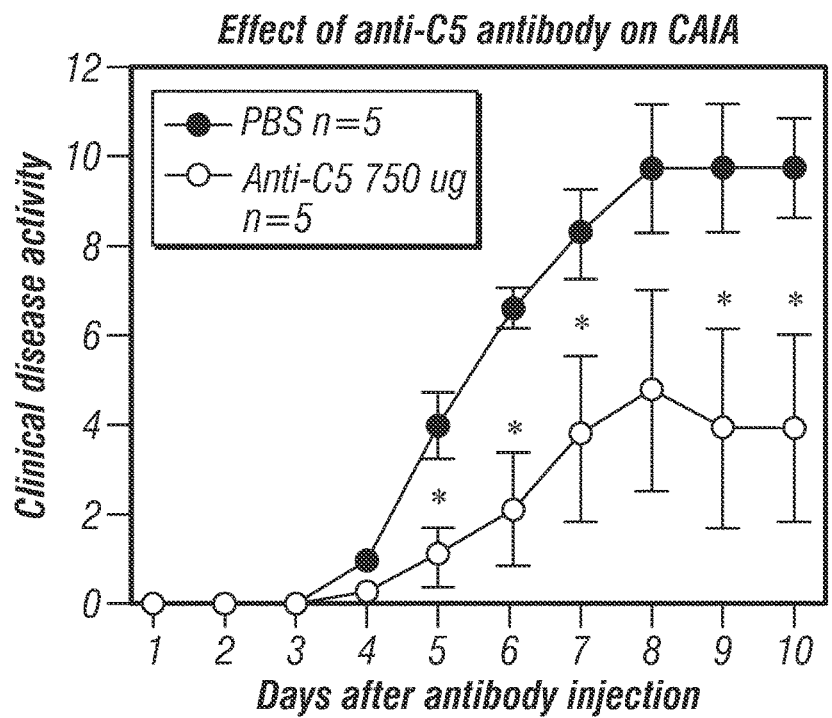

The inventors and others have demonstrated the importance of complement in arthritis (Banda et al., 2007 and Banda et al., 2006) (also see (Arend and Firestein, 2012 and Happonen et al., 2012). Focusing on the CAIA model, they found that knockout of C3aR leads to a decrease in disease intensity while knockout of C5aR virtually blocks disease (FIG. 2A) (Banda et al. 2012). C6 is required for MAC formation and C6 deficient mice showed decreased disease development as well (FIG. 2B). They measured C5a levels in serum samples from these mice both before and after CAIA induction and found no change, suggesting that C5 production from outside the joint is not increased in this disease model (data not shown). To determine the requirement for C5 in CAIA, the inventors made use of a blocking anti-C5 antibody (unpublished data). Mice were dosed with 750 μg of antibody on days 3 and 7. As shown in FIG. 2D, disease activity was decreased however this decrease was less than that seen with C5aR gene disruption (compare FIG. 2A with FIG. 2D). This is consistent with the inventors' observations of the effects of this antibody in the CIA model (Banda et al., 2012). C5L2 is a second more recently identified receptor which engages C5a. However, its role remains unclear (Li et al., 2013). As shown in FIG. 2C, the inventors examined the function of C5L2 receptors within the CAIA model using C5L2 knockout mice and found that disease was unaffected, suggesting that this receptor is not a useful target (unpublished data). The inventors interpret these data as demonstrating that while blockade of the C5 pathway has profound effects on the development of disease, antibody mediated sequestration is not sufficient to fully inhibit this pathway.

Figure 5A:
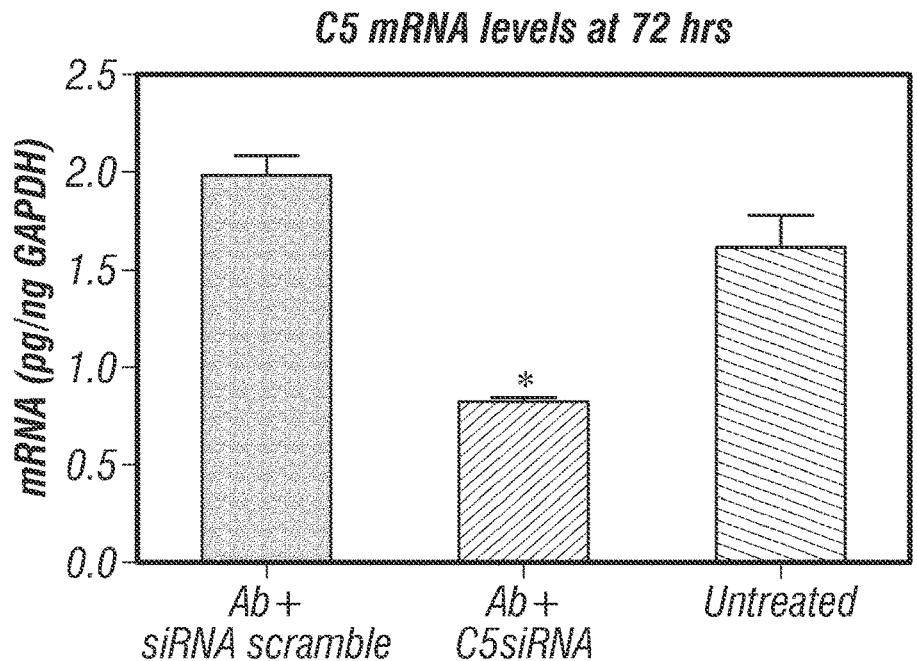
FIGS. 5A-5B. Specificity of C5 siRNA. RAW 264.7 cells were pretreated with C5aRAb and transfected with either a control siRNA (scramble) or C5 siRNA. After 72 hours mRNA levels for C5 (FIG. 5A), C5aR (FIG. 5B), and GAPDH were determined by qPCR using Taqman probes. Control was not treated with Ab or siRNA. Exact amounts determined by standard curves generated with synthetic cDNAs.
Figure 5B:
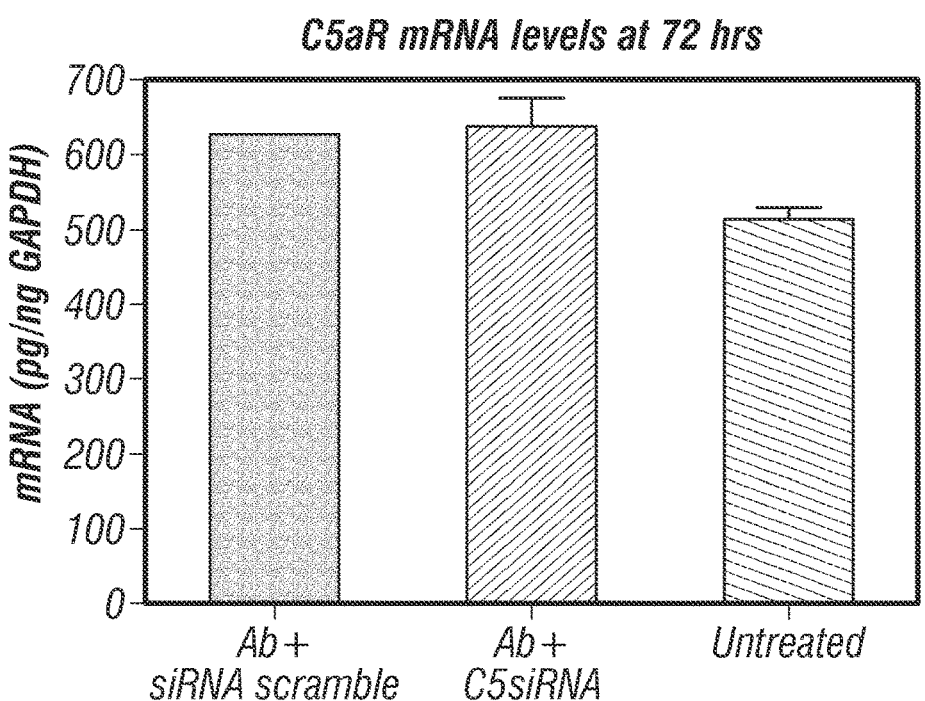

The inventors then began to address their hypotheses with a number of critical experiments. They purchased an anti-C5aR antibody (clone 20/70, C5aR-Ab) from LifeSpan Biosciences. This clone has been well described as an anti-C5aR blocking antibody by several investigators (Godau et al., 2004; Shagdarsuren et al., 2010; Shushakova et al., 2002; Soruri et al., 2003 and Wang et al., 2013) as well as in U.S. Pat. No. 8,337,852. It functions by binding to C5aR and stearically inhibiting the interaction of C5a with its receptor. They first successfully conjugated protamine to C5aR-Ab as shown in FIG. 3. Conjugation was performed by BIOO Scientific with approximately 30% efficiency. Second, they confirmed by FACS analysis that conjugation has no effect on the ability of C5aR-Ab to bind to the C5aR (FIG. 4). Third, they confirmed that C5siRNA knock-down is specific for C5 mRNA in RAW cells. Since RAW cells express both C5 and C5aR, the inventors replicated some aspects of proposed in vivo studies by first pre-treating $1\times10^5$ cells with 10 μg C5aR-Ab/well and then transfected these cells with 5 μM of either control (scramble) or C5siRNA. All cells were harvested after 72 hrs and RNA was prepared for the qRTPCR. The inventors found that C5 siRNA knocked down C5 mRNA levels with no effect on C5aR mRNA abundance (FIGS. 5A-B). Likewise, pretreatment with C5aR-Ab had no effect on C5 or C5aR mRNA levels.

Figure 6:
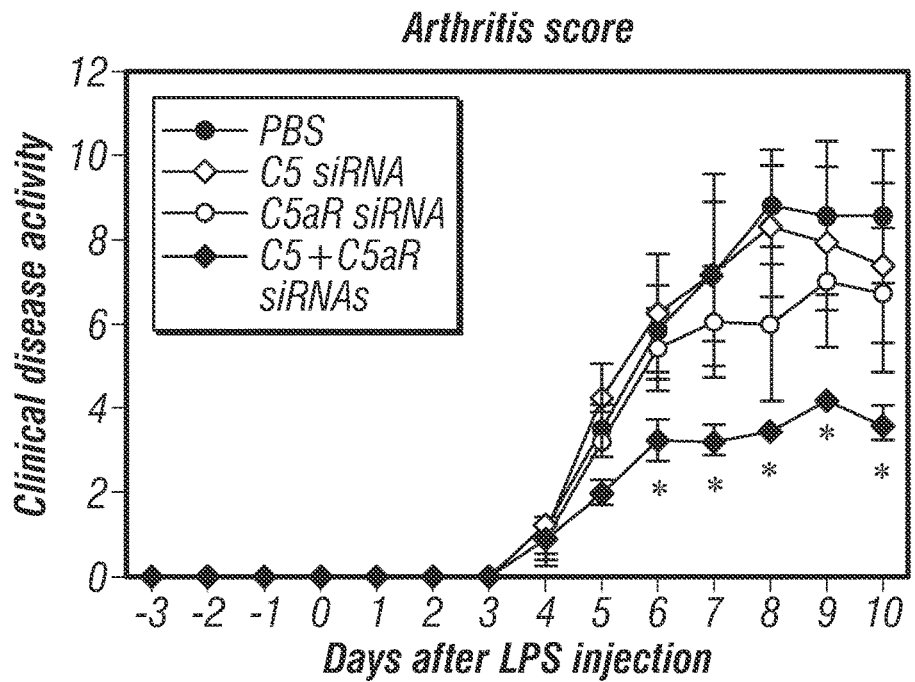
FIG. 6. Treatment of CAIA with Accel® siRNAs against C5 and C5aR. Groups of 5 mice were input into the CAIA model and treated with intravenous injections of either PBS, C5siRNA (8 µg), C5aR siRNA (8 µg, closed squares), or a combination of C5siRNA and C5aR siRNA (16 µg, open squares). Disease was read by a blinded observer.

The inventors performed two in vivo studies to assess and characterize the efficacy of their complex. In the initial study, they used Accel® siRNA (Dharmacon) chemically modified to be nuclease resistant, resulting in prolonged serum half-life. Specificity was confirmed as above (FIG. 5A-5B and data not shown). They included 4 groups of 5 animals in the CAIA model. Groups received intravenous injections of either PBS, 8 μg Accel® C5siRNA, 8 μg Accel® C5aRsiRNA, or a combination of both siRNAs (16 μg). The injections were given on days −5, 0, and 3 relative to injection of pathogenic antibodies. It is important to point out that the two siRNAs are completely independent and partition into cells independently. Clinical scoring was performed as described previously (Banda et al., 2006). As shown in FIG. 6, C5aRsiRNA and C5siRNA alone had minimal effects as compared to control (PBS), while the combination of both siRNAs reduced clinical disease activity by approximately 50%.

Figure 7A:
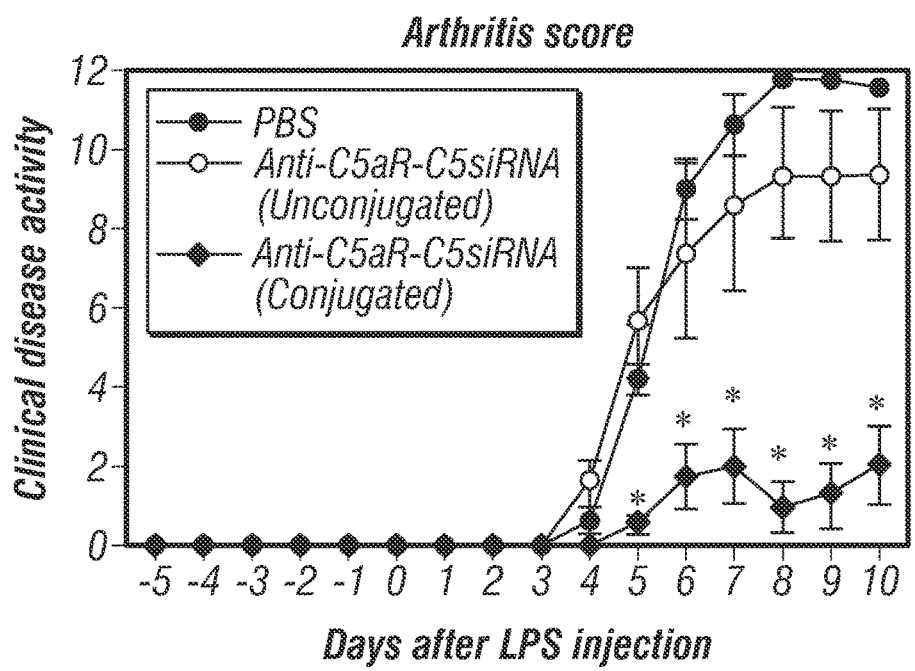
FIGS. 7A-7B. Treatment of CAIA with Anti-C5aR-05siRNA complexes.
Figure 7B:
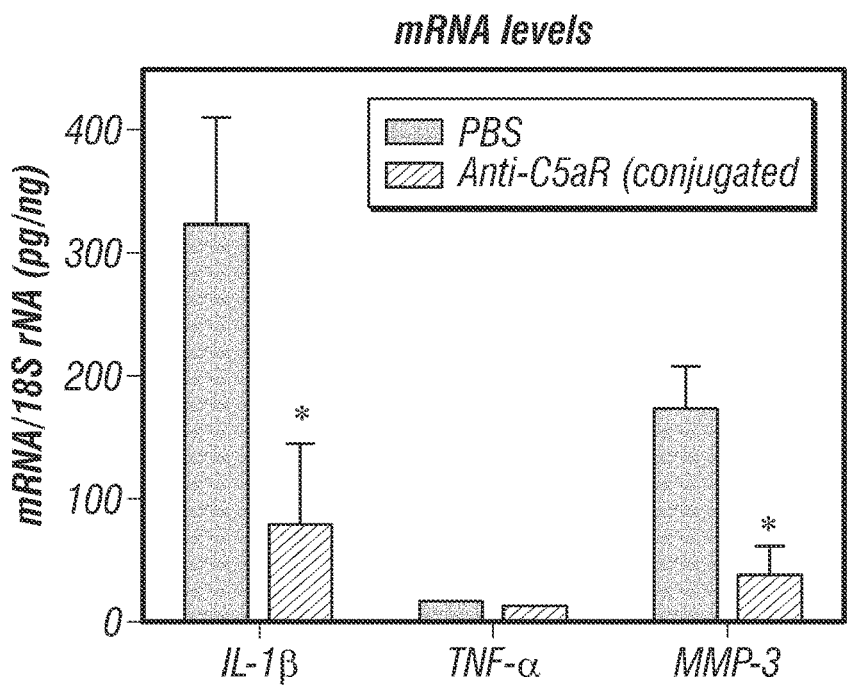
Figure 8A:
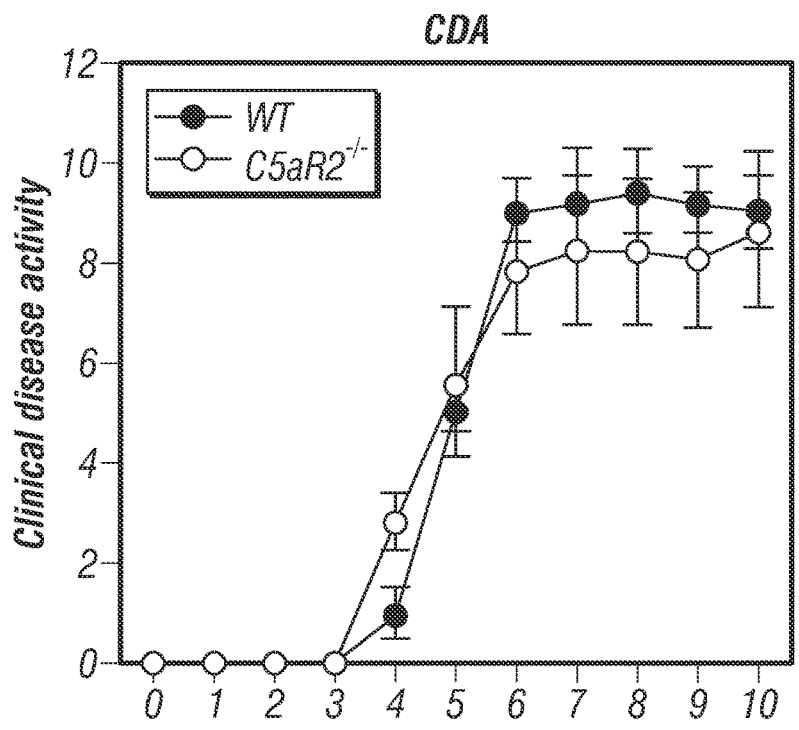
FIGS. 8A-8F. C5aR2 is not involved in CAIA but anti-C5 mAb, commercially available C5 and C5aR1 siRNAs affected the CDA in CAIA.
Figure 8B:
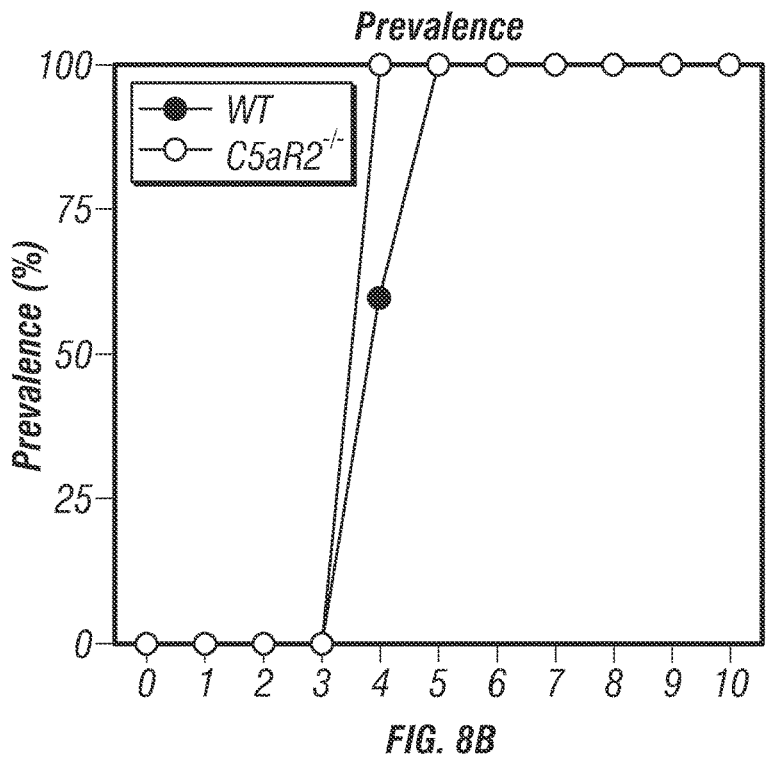
Figure 8C:
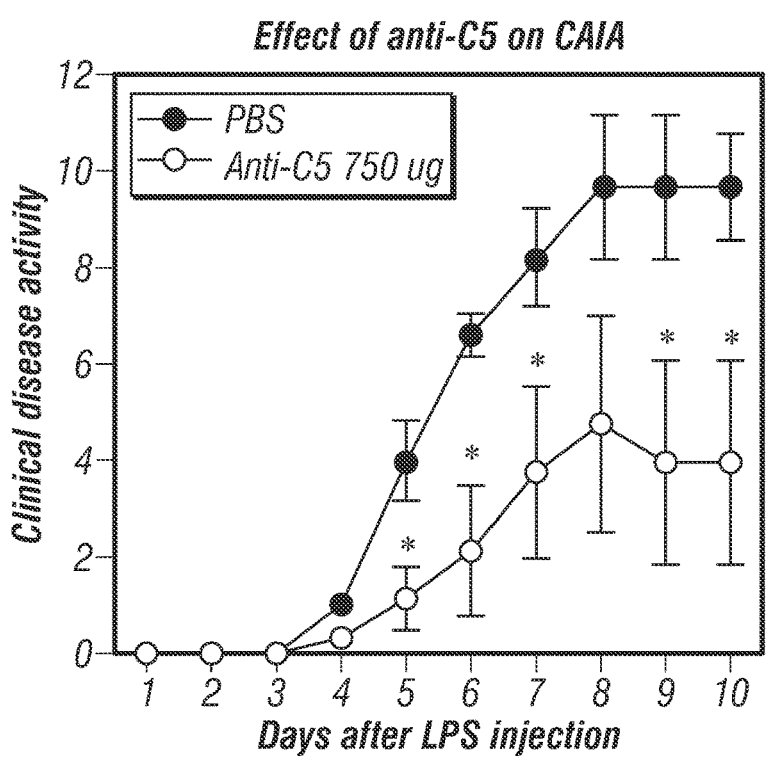
Figure 8D:
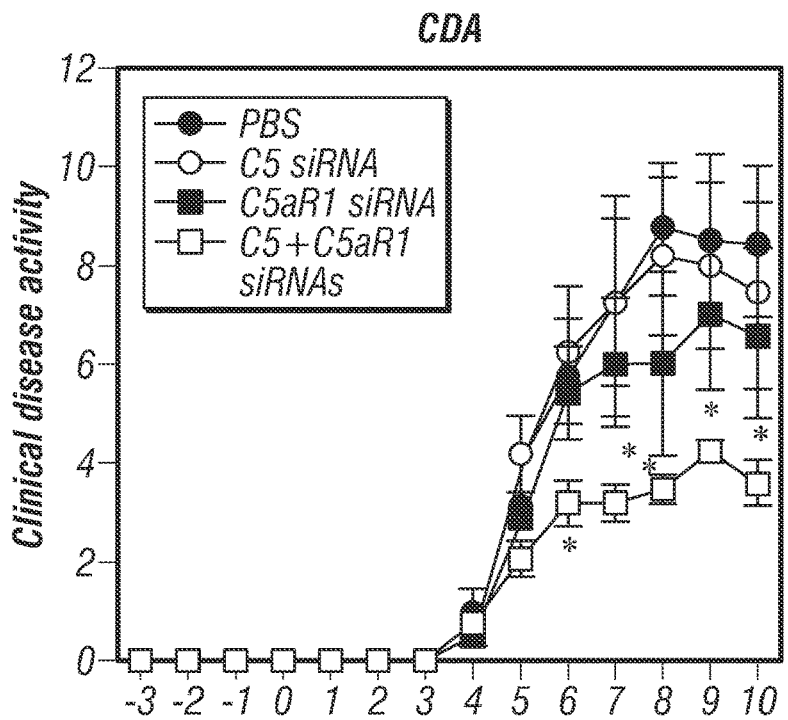
Figure 8E:
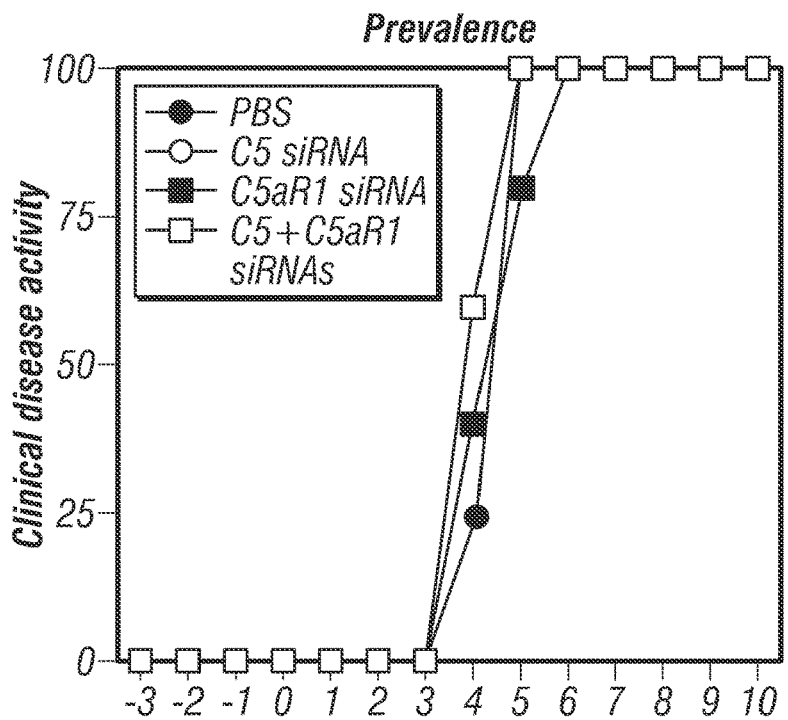
Figure 8F:
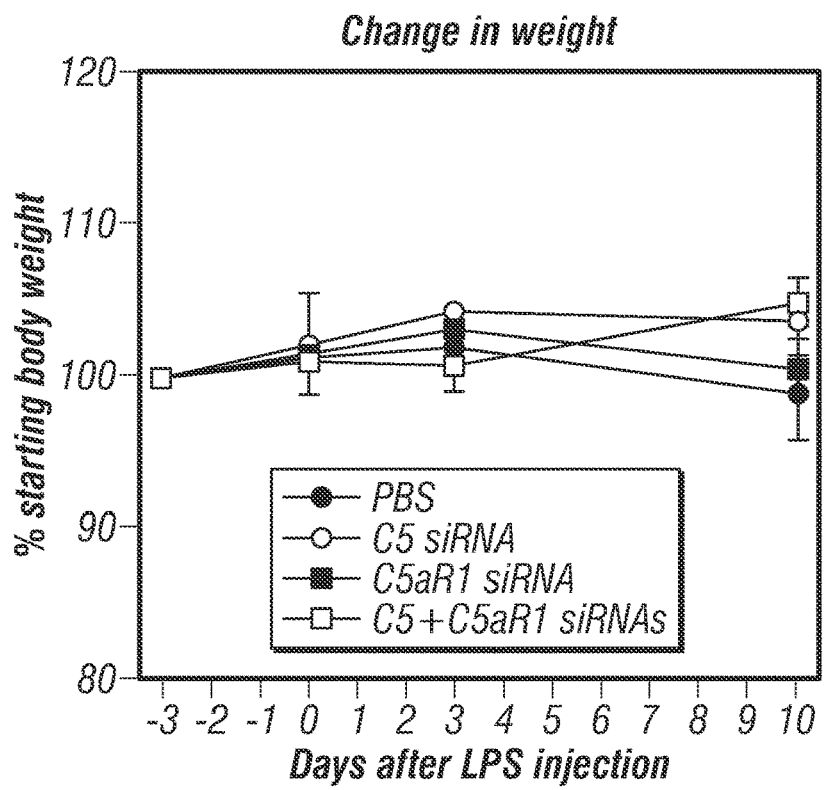
Figure 9A:
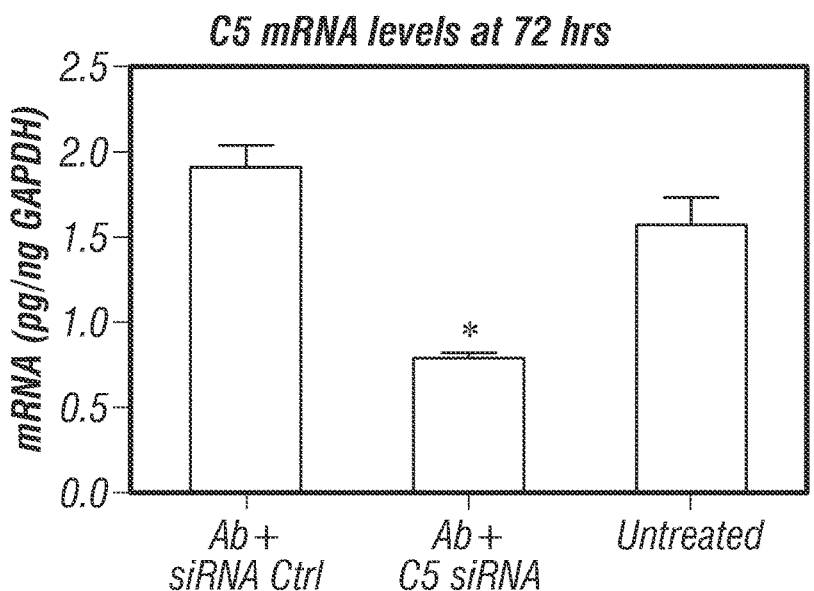
FIGS. 9A-9D. Specificity of C5 siRNA for C5 mRNA used to conjugate with protamine-anti-C5aR1 mAb (20/70). C5 siRNA specifically inhibited mRNA for C5 not for C5aR1. RAW cells were pretreated with C5aR mAb and transfected with either a control siRNA (scramble) or C5 siRNA. A mixture of four C5 siRNA was used for these studies. After 72 hours of culturing transduced RAW cells the mRNA levels for C5, C5aR1, and GAPDH were determined by qRT-PCR using Taqman probes. Control RAW cells (untreated) were not treated with anti-C5aR1 mAb or C5 siRNA.
Figure 9B:
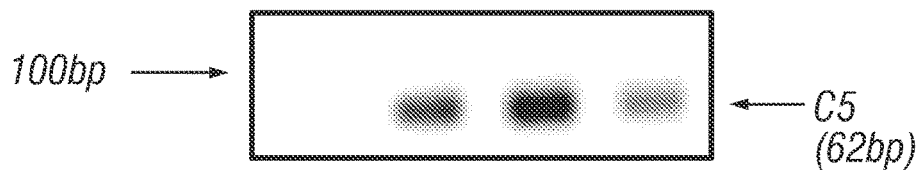
Figure 9C:
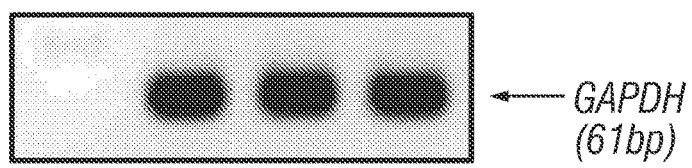
Figure 9D:
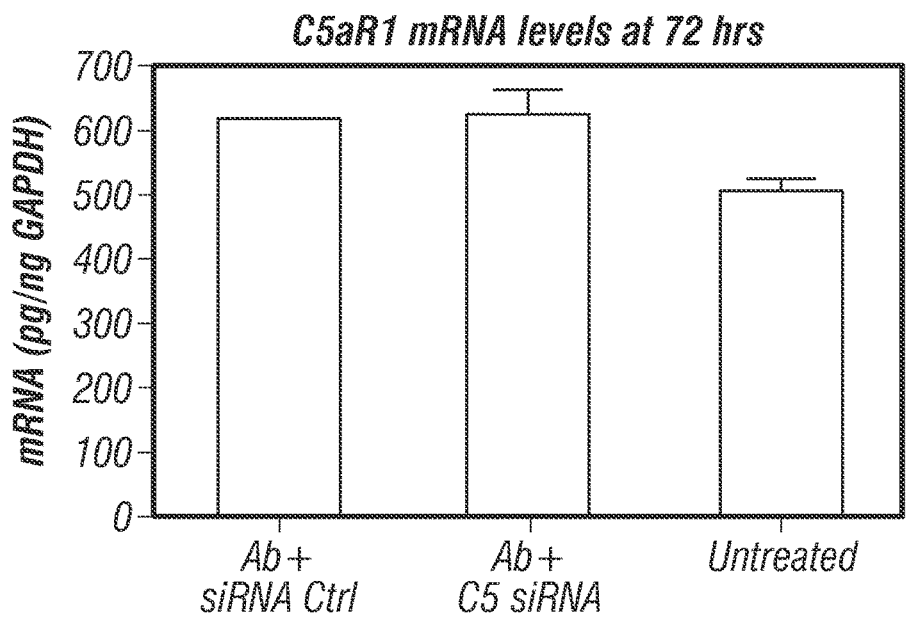
Figure 10A:
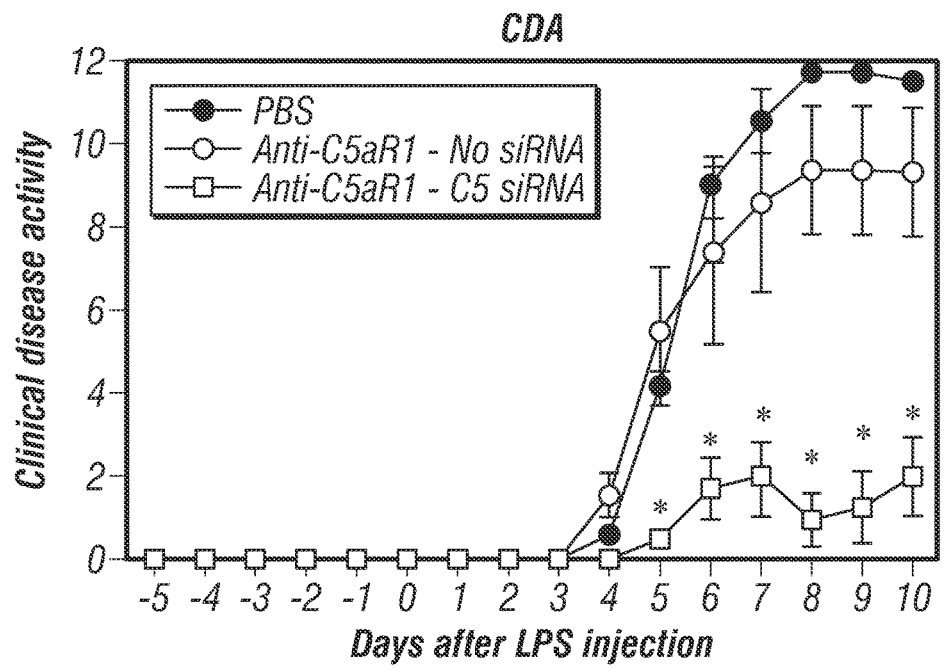
FIGS. 10A-10F. Effect of anti-C5aR1-protamine-05 siRNA on CAIA CAIA was inhibited by injecting a conjugate of anti-C5aR1 mAb-protamine-05 siRNA but not by a unconjugate of anti-C5aR-protamine without C5 siRNA. Groups of 5 mice were input into the CAIA model and treated mice with PBS or a conjugate of anti-C5aR1 mAb-protamine-05 siRNA (150 µg anti-C5aR1 mAb-8 µg C5 siRNA/mouse/i.p.) or with a conjugate of anti-C5aR mAb—no protamine—C5 siRNA (150 µg anti-C5aR1 mAb-8 ug C5 siRNA/mouse/i.p.).
Figure 10B:
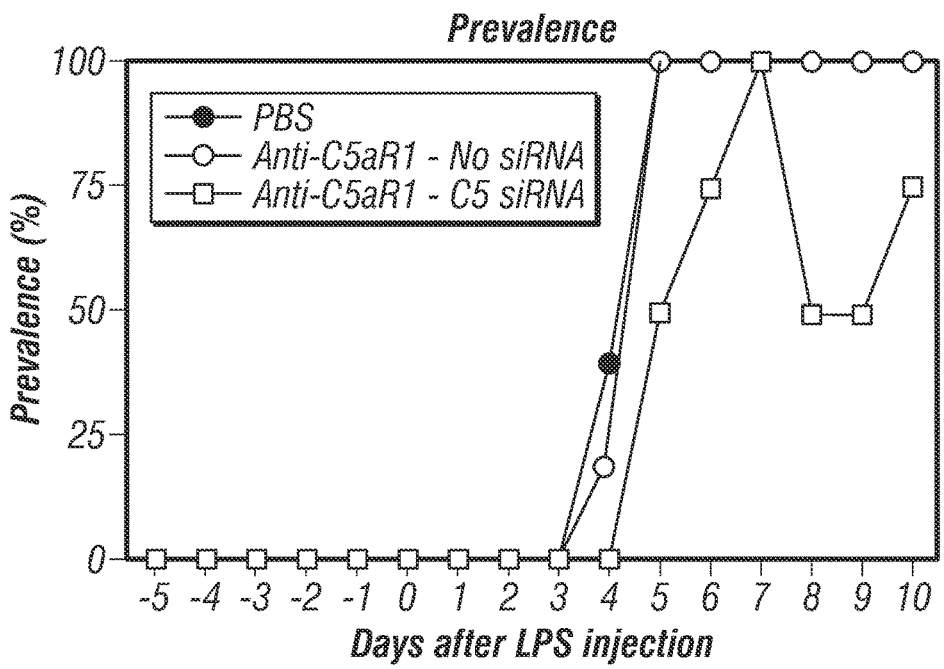
Figure 10C:
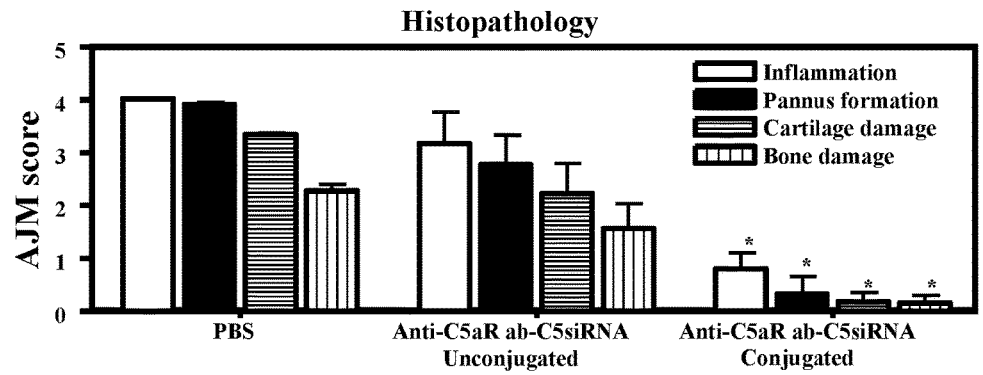
Figure 10D:
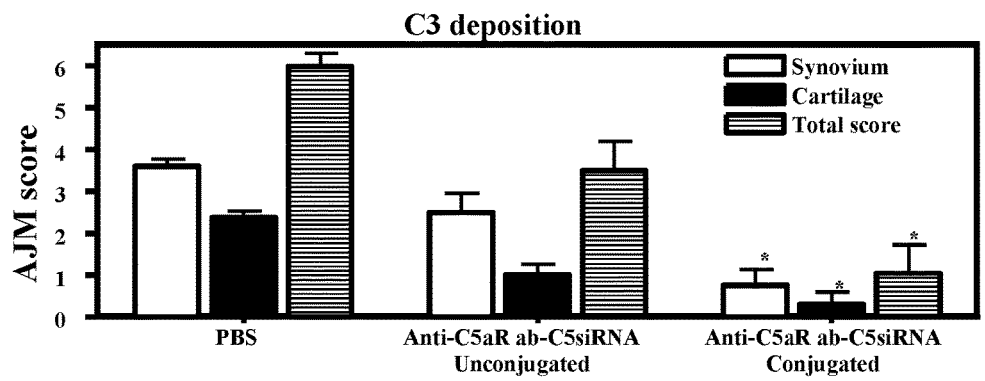
Figures 10E, 10F:
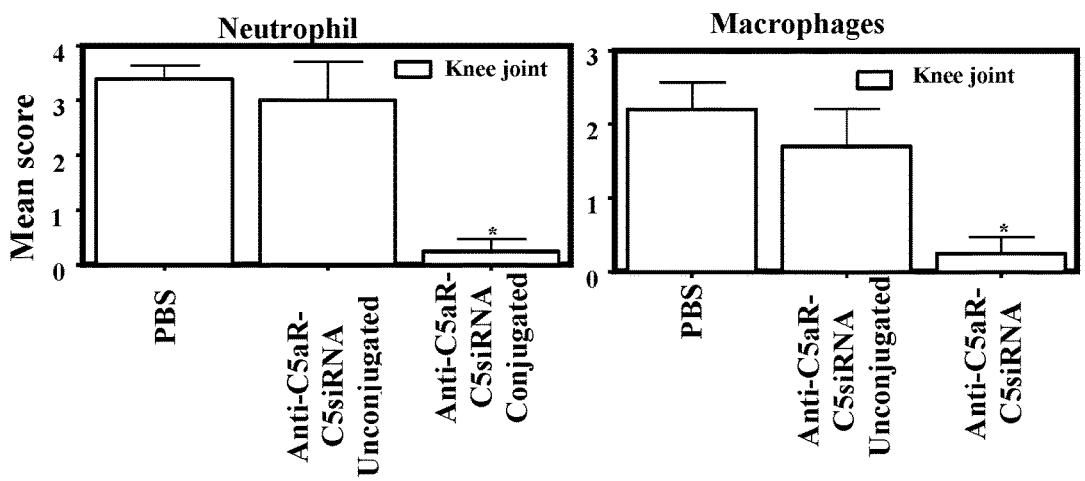

In the second study, the inventors examined the efficacy of their Ab-siRNA complex. Again, mice were included in the CAIA model. Groups (N=5) received intraperitoneal injections of either PBS, a mix of 150 μg C5aR-Ab (unconjugated) plus 8 μg C5siRNA, or the same amounts of C5aR-Ab (conjugated to protamine) plus C5siRNA such that they formed a complex upon mixing. Again, injections were given on days −5, 0 and 3 as above. As shown in FIGS. 7A-7B, the mixture of unconjugated C5aR-Ab+C5siRNA had only a minimal effect on disease progression while the complex reduced clinical disease activity by 82%. Additionally, it is important to note that modified siRNAs do not efficiently bind to the complex, and thus the inventors used unmodified siRNAs for this study. Weight loss was greater in PBS and unconjugated treatment groups as compared to the conjugation treatment group indicating improved mobility and appetite (data not shown). The inventors measured mRNA levels for various inflammatory proteins including IL-1β, TNFα, and MMP3 (FIG. 7B). Collectively these data suggest that (i) the antibody and siRNA components are active and specific for their targets and (ii) targeting of both C5 production and C5aR signaling appears to be synergistic (whether by siRNA or by Ab-siRNA complex), and (iii) the complex of antibody plus siRNA (which includes a suboptimal dose of antibody and unmodified C5siRNA) is far superior to any other treatment condition (including modified siRNAs) tested in this series.

Example 2

Proposed Methodologies

FIG. 1 illustrates the first method of constructing the siRNA-IgG complex as described by Hauser et al. (Hauser et al., 2010). It consists of a monovalent IgG fragment generated by 2-MEA cleavage. Upon removal of 2-MEA with a desalting column NeutrAvidin (deglycosylated avidin) is conjugated to the now available sulfhydryl group. Biotinylated protamine (via its N-terminal amino group) is then attached. The tetrameric form of NeutrAvidin allows multiple protamine molecules to bind. Protamine functions as the siRNA carrier. This method of construction has been reported to have the advantages of (a) not itself activating complement (as it cannot support the formation of CO and (b) being smaller and more mobile than the divalent antibody. The second method of constructing the siRNA-IgG complex involves amine conjugation to a standard divalent IgG. BIOO Scientific (Austin, Tex.) has developed a proprietary technology in which a large fragment of protamine is placed in a buffer environment such that it can be amine conjugated to IgG. Conjugation is not targeted and is dependent on the number and accessibility of lysines in the protein. BIOO estimates that on average, 3 protamine molecules are bound to an IgG after conjugation and that 1 protamine fragment can bind 20-30 siRNAs (Lance Ford, BIOO Scientific, personal communication). The advantage of this method of construction is that the fewer steps are involved leading to decreased loss of material and that binding properties of the antibody generally remain unaltered. The data shown in FIGS. 3, 4, and 7 were generated using a complex prepared by this second method.

Monovalent siRNA-IgG complexes may be produced by the method of Hauser et al. (Hauser et al., 2010) as described above. In brief, the inventors will treat 50 µg of anti-C5aR IgG (clone 20/70) with 50 mM 2-MEA. After desalting, the inventors will then link NeutrAvidin to the free sulfhydryl group using the EZ-Link® kit as per the manufacturer's instructions (EZ-Link® Maleimide Activated NeutraAvidin™ Protein, Pierce Chemicals, Rockford Ill.). Protamine sulfate (Salmine P4020, Sigma, St. Louis Mo.) will be biotinylated at its N-terminal amino group using the Pierce EZ-Link® Sulfo-NHS-Biotinylation kit as per manufacturer's instructions. Antibody and protamine will then be mixed at ratios of 1:1, 1:2, and 1:3 (rotated at 4° C. for 60 min). Conjugation efficiency will be assessed by size exclusion chromatography using the 1:3 reaction.

Amine conjugation of protamine to divalent C5aR-Ab may be performed using the BIOO T3-Max® Conjugation kit according to the manufacturer's instructions. In brief, the antibody is dialyzed and combined with kit components at a specific temperature. The coupling reaction is affected by the relative masses of protamine and antibody, reaction temperature, and reaction time. The inventors will perform test conjugations with 50 µg of C5aR-Ab. The conjugation reaction runs for 14-16 hrs followed by addition of buffer which both stops the reaction and places the complex in an environment suitable for siRNA loading and in vivo administration. As the conjugation conditions have been optimized for general usage it is likely that further optimization will improve yield (Lance Ford, BIOO Scientific, personal communication). The inventors will vary temperature, protamine/antibody ratios, and reaction times to find a reaction optimum.

For both complexes, siRNA loading involves an identical process. Complex is incubated with siRNA at 4° C. for 30 min. Loading capacity of each complex will be tested. Increasing amounts of FITC labeled siRNA will be loaded onto a known amount of each complex in a 96-well plate format. Fluorescence will then be measured. Numbers of siRNA molecules loaded per molecule of complex will be calculated using an siRNA fluorescence standard curve. After removal of unconjugated protamine by gel filtration chromatography, complexes will be assessed by SDS-PAGE and protamine Western blotting. Conjugation efficiency will be determined by the amount of material which has increased in molecular weight (see FIG. 3) and by the protamine signal.

Conjugated IgG will be mixed with siRNA at molar ratios ranging from 1:5-1:100 (IgG complex: siRNA) in a 96-well plate format. Complexes will then be tested in RAW cells as follows. Antibody complex (500 ng) will be added per well. Controls will include conjugated antibody without siRNA and siRNA alone. In initial experiments to optimize molar ratios, conjugated antibody and/or siRNA will be added to wells in serum free media and allowed to interact for 15 min. Cells will then be added and the plate incubated overnight. After aspiration and replacing of the media, the cells will be incubated for an additional 48 hours. Knockdown of mRNA will then be assessed by quantitative PCR using a Taqman probe system (FIGS. 5A-5B). C5 protein will be measured by Western Blotting. C5aR expression will also be assessed in other experiments by flow Cytometry as a specificity control. The molar ratio of IgG to siRNA which provides the greatest knockdown will be calculated (possible range: 210 ng to 3.8 µg siRNA per 500 ng IgG).

To demonstrate targeting, the inventors will similarly load a control mouse IgG with C5siRNA and demonstrate that the specificity of the antibody is crucial to the success of knockdown. In other versions of this experiment, Fc block will be used in combination with C5siRNA-antiC5aR-Ab complex to explore the degree of uptake via Fc receptors. The inventors will also screen for IFNγ production to assess if the siRNA-Ab complex inadvertently activates TLR3.

\*\*\*

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VI. References

The following references, to the extent that they provide exemplary procedural or other details supplementary to those set forth herein, are specifically incorporated herein by reference.

Andersson et al., *Immunology*, 73(2): p. 191-6, 1991.
Arend and Firestein, *Nat Rev Rheumatol*, 8(10): p. 573-86, 2012.
Ballanti et al., *Immunol Res*, 56(2-3): p. 477-91, 2013.
Banda et al., *Arthritis Rheum*, 46(11): p. 3065-75, 2002.
Banda et al., *Clin Exp Immunol*, 159(1): p. 100-8, 2010.
Banda et al., *J Immunol*, 177(3): p. 1904-12, 2006.
Banda et al., *J Immunol*, 179(6): p. 4101-9, 2007.
Banda et al., *J Immunol*, 188(3): p. 1469-78, 2012.
Banerjee et al., *J Immunol*, 142(7): p. 2237-43, 1989.
Beidler et al., *J. Immunol.*, 141(11):4053-4060, 1988.
Bosher and Labouesse, *Nat. Cell. Biol.*, 2:E31-E36, 2000.
Campbell et al., *Am. Rev. Respir. Dis.*, 130(3):417-423, 1984.
Caplen et al., *Gene*, 252(1-2):95-105, 2000.
Cross et al., *Ann Rheum Dis*, 73(7): p. 1316-22, 2014.
Elbashir et al., *Nature*, 411(6836):494-498, 2001.
EP Application 125,023
EP Application 171,496
EP Application 173,494
EP Application 184,187
Fire et al., *Nature*, 391:806-811, 1998.
Gefter et al., *Somatic Cell Genet.*, 3:231-236, 1977.
Godau et al., *J Immunol*, 173(5): p. 3437-45, 2004.
Goding, In: *Monoclonal Antibodies: Principles and Practice*, 2d ed., Academic Press, Orlando, Fla., pp 60-61, 71-74, 1986.
Grishok et al., *Science*, 287:2494-2497, 2000.
Guo et al, *Annu Rev Immunol*, 23: p. 821-52, 2005.
Haas and van Strijp, *Immunol Res*, 37(3): p. 161-75, 2007.
Happonen et al., *Immunobiology*, 217(11): p. 1088-96, 2012.
Harlow and Lane, In: *Antibodies: A Laboratory Manual*, Cold Spring Harbor Laboratory, 1988.
Hauser et al., *PLoS One*, 5(3): p. e9463, 2010.
Hill et al., *Blood*, 106(7): p. 2559-65, 2005.
Humbles et al., *Nature*, 406(6799): p. 998-1001, 2000.
Hwang et al., *Crit. Rev. Ther. Drug Carrier Syst.*, 15(3): 243-284, 1998.
Jones et al., *Nature*, 321:522-525, 1986.
Ketting et al., *Cell*, 99:133-141, 1999.
Kohl and Wills-Karp, *Curr Opin Pharmacol*, 7(3): p. 283-9, 2007.
Kohler and Milstein, *Eur. J. Immunol.*, 6:511-519, 1976.
Kohler and Milstein, *Nature*, 256:495-497, 1975.
Lee et al., *Immunol Cell Biol*, 86(2): p. 153-60, 2008.
Li et al., *Faseb J*, 27(3): p. 855-64, 2013.
Lim et al., *FASEB J*, 27(2): p. 822-31, 2013.
Lin and Avery, *Nature*, 402:128-129, 1999.
Macor et al., *Arthritis Rheum*, 64(8): p. 2559-67, 2012.
Markiewski et al., *Nat. Immunol*, 9(11): p. 1225-35, 2008.
Mathiowitz et al., *Nature*, 386(6623):410-414, 1997.
Montgomery et al., *Proc. Natl. Acad. Sci. USA*, 95:155-2-15507, 1998.
Morrison, *Science*, 229(4719):1202-1207, 1985.
Nandakumar et al., *PLoS One*, 5(10): p. e13511, 2010.
Neumann et al., *Arthritis Rheum*, 46(4): p. 934-45, 2002.
Onuma et al., *Rheumatol Int*, 22(2): p. 52-5, 2002.
PCT Appln. PCT/US86/02269
PCT Appln. WO 86/01533
Pincus et al., *Arthritis Rheum*, 27(8): p. 864-72, 1984.
Posner et al., *Hybridoma* 6, 611-625, 1987.
Remington's Pharmaceutical Sciences, 15th ed., pages 1035-1038 and 1570-1580, Mack Publishing Company, Easton, Pa., 1980.
Remington's Pharmaceutical Sciences, 18th Ed. Mack Printing Company, pp. 1289-1329, 1990.
Schieferdecker et al., *Int Immunopharmacol*, 1(3): p. 469-81, 2001.
Shagdarsuren et al., *Circulation*, 122(10): p. 1026-36, 2010.
Sharp and Zamore, *Science*, 287:2431-2433, 2000.
Sharp, *Genes Dev.*, 13:139-141, 1999.
Shaw et al., *J. Natl. Cancer Inst.*, 80(19):1553-1559, 1988.
Shushakova et al., *J Clin Invest*, 110(12): p. 1823-30, 2002.
Sokka et al., *J Rheumatol*, 26(8): p. 1681-5, 1999.
Soruri et al., *Immunol Lett*, 88(1): p. 47-52, 2003.
Spinella et al., *Immunogenetics*, 34(1): p. 23-7, 1991.
Sun et al., *J. Steroid Biochem.*, 26(1):83-92, 1987.
Tabara et al., *Cell*, 99:123-132, 1999.
U.S. Pat. No. 4,196,265
U.S. Pat. No. 4,415,723
U.S. Pat. No. 4,458,066
U.S. Pat. No. 4,554,101
U.S. Pat. No. 4,816,567
U.S. Pat. No. 4,867,973
U.S. Pat. No. 5,399,363
U.S. Pat. No. 5,466,468
U.S. Pat. No. 5,543,158
U.S. Pat. No. 5,565,332
U.S. Pat. No. 5,580,579
U.S. Pat. No. 5,629,001
U.S. Pat. No. 5,641,515
U.S. Pat. No. 5,792,451
U.S. Pat. No. 5,795,715
U.S. Pat. No. 5,889,136
U.S. Pat. No. 6,074,674
U.S. Pat. No. 6,270,750
U.S. Pat. No. 6,537,514
U.S. Pat. No. 6,613,308
U.S. Pat. No. 6,936,270
Vergunst et al., *Rheumatology (Oxford)*, 46(12): p. 1773-8, 2007.
Verhoeyen et al., *Science*, 239(4847):1534-1536, 1988.
Wang et al., *J Immunol*, 191(8): p. 4001-9, 2013.
Wang et al., *Proc Natl Acad Sci USA*, 92(19): p. 8955-9, 1995.
Wincott et al., *Nucleic Acids Res.*, 23(14):2677-2684, 1995.
WO 01/36646
Wood et al., *J. Clin. Lab. Immunol.*, 17(4):167-171, 1985.
Woodruff et al., *Mol Immunol*, 48(14): p. 1631-42, 2011.
Yuan et al., *Chin Med J (Engl)*, 116(9): p. 1408-12, 2003.

The invention claimed is:

1. A composition comprising anti-C5a receptor (C5aR) (clone 20/70) antibody that is conjugated to a siRNA that silences C5a expression.

2. The composition of claim 1, wherein said antibody is conjugated to said siRNA by a linker.

3. The composition of claim 2, wherein said linker is a cleavable linker.

4. The composition of claim 3, wherein said cleavable linker is cleaved by an intracellular or extracellular enzyme.

5. The composition of claim 2, wherein said linker comprises biotin/avidin.

6. The composition of claim 3, wherein said antibody is humanized.

7. The composition of claim 1, further comprising at least one selected from the group consisting of an inhibitor of C5b, a second inhibitor of C5a, an inhibitor of C3a or C3b, and a rheumatoid arthritis therapeutic agent.

8. A method of treating rheumatoid arthritis in a human subject, the method comprising administering to said subject a composition comprising humanized anti-C5a receptor (C5aR) (clone 20/70) antibody that is conjugated to a siRNA that silences C5a expression.

9. The method of claim 8, wherein said antibody is conjugated to said siRNA by a linker.

10. The method of claim 8, wherein said linker is a cleavable linker.

11. The method of claim 10, wherein said cleavable linker is cleaved by an intracellular or extracellular enzyme.

12. The method of claim 10, wherein said linker comprises biotin/avidin.

13. The method of claim 10, wherein said cleavable linker is cleaved by an agent or treatment exogenous to said subject.

14. The method of claim 8, further comprising administering at least one selected from the group consisting of an inhibitor of C5b, a second inhibitor of C5a, an inhibitor of C3a or C3b, and a rheumatoid arthritis therapeutic agent.

15. The method of claim 8, wherein administration comprises oral administration, vascular administration, or intra-articular injection.

16. The method of claim 8, wherein said administration of said composition to said subject is performed at least twice.

17. The method of claim 16, wherein said administration comprises daily, every other day, every third day, bi-weekly weekly, bi-monthly or monthly administration.

18. The method of claim 8, wherein said treatment results in at least one effect selected from the group consisting of reduced joint pain in said subject, greater joint range of motion in said subject, and greater mobility for said subject.

19. The composition of claim 1, wherein the linker comprises protamine.

20. The method of claim 8, wherein the linker comprises protamine.

* * * * *